United States Patent [19]
Su et al.

[11] Patent Number: 5,985,863
[45] Date of Patent: Nov. 16, 1999

[54] COMPOSITIONS AND METHODS FOR DECREASING IGIF AND IFN-γ PRODUCTION BY ADMINISTERING AN ICE INHIBITOR

[75] Inventors: Michael Su, Newton; Yong Gu, Brookline; David J. Livingston, Newtonville, all of Mass.

[73] Assignee: Vertex Pharmaceuticals, Inc., Cambridge, Mass.

[21] Appl. No.: 08/712,878

[22] Filed: Sep. 12, 1996

[51] Int. Cl.$^6$ ............................ A61K 31/33; A61K 31/55
[52] U.S. Cl. ...................... 514/183; 514/221; 514/814; 514/825; 514/826; 514/863; 514/866; 514/894; 514/903
[58] Field of Search ......................... 514/183, 221, 514/814, 825, 826, 863, 866, 894, 903

[56] References Cited

U.S. PATENT DOCUMENTS 5,656,627  8/1997  Bemis et al. ............................ 514/221

OTHER PUBLICATIONS

J. Fernando Bazan, "A Newly Defined Interleukin–1?", *Nature,* 379, p. 591 (Feb., 1996).

*Primary Examiner*—Kimberly Jordan
*Attorney, Agent, or Firm*—Fish & Neave; James F. Haley, Jr.; Lisa A. Dixon

[57] ABSTRACT

The present invention relates to methods and pharmaceutical compositions for decreasing the production of interferon-gamma inducing factor (IGIF). The invention also relates to methods and pharmaceutical compositions for decreasing the production of interferon-gamma (IFN-γ). The compositions comprise a therapeutically effective amount of a compound which inhibits interleukin-1β converting enzyme (ICE) and a pharmaceutically acceptable carrier. The methods comprise the step of administering the above compositions to a subject. The present invention also relates to methods for treating or reducing the advancement, severity or effects of an IGIF- or IFN-γ-mediated inflammatory, infectious or autoimmune condition.

17 Claims, 35 Drawing Sheets

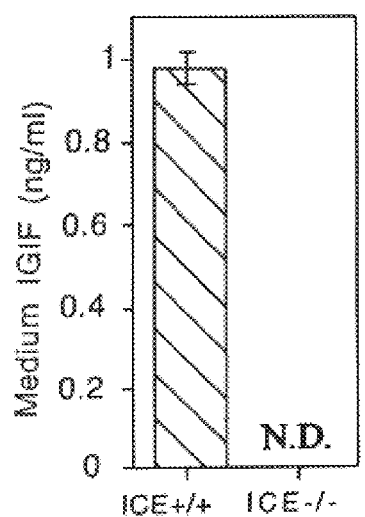
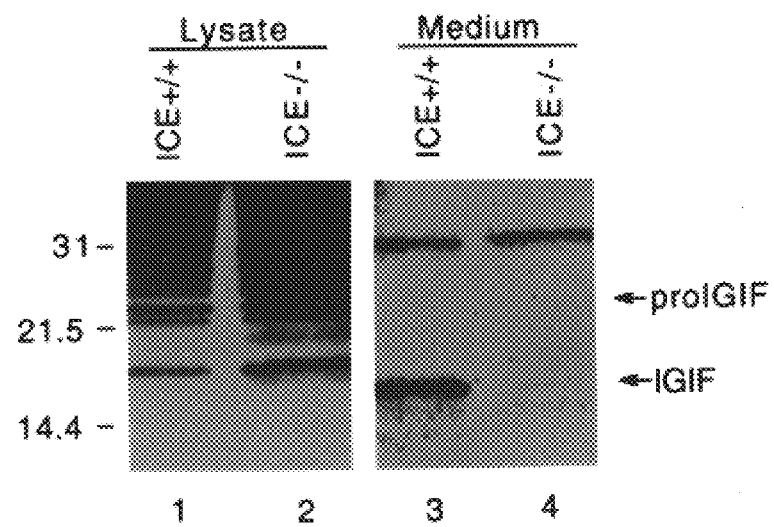
FIG. 3A   FIG. 3B
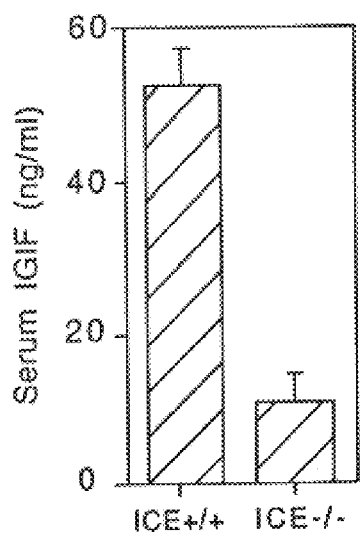
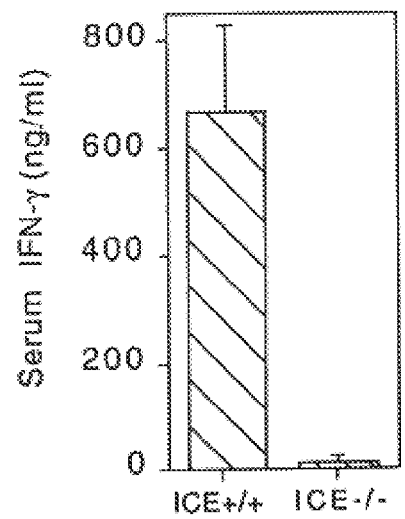
FIG. 3C   FIG. 3D

Figure 6

| Compound | Structure | Compound | Structure |
|---|---|---|---|
| 213e | 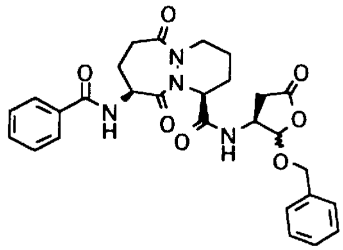 | 1036 | 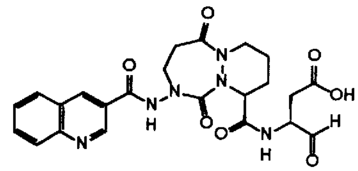 |
| 214c | 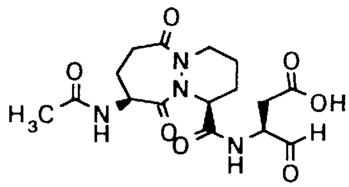 | 1037 | 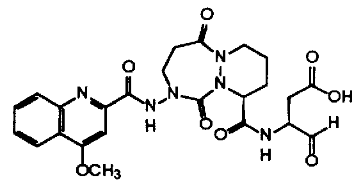 |
| 214e | 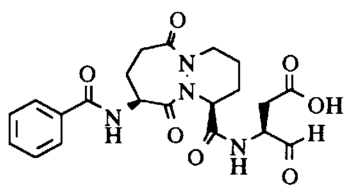 | 1038 | 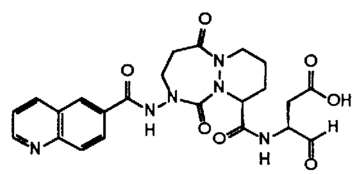 |
| 217c | 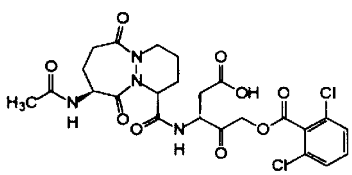 | 1039 | 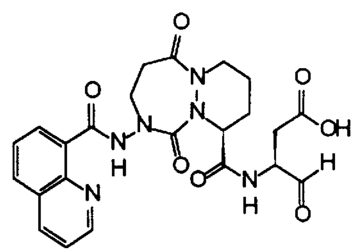 |
| 217d | 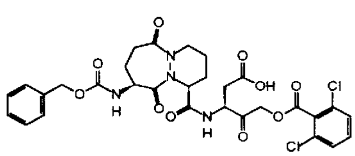 | 1040 | 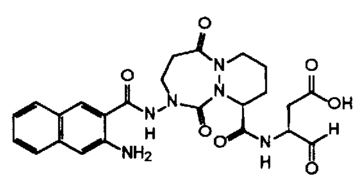 |

| Compound | Structure | Compound | Structure |
|---|---|---|---|
| 227e | 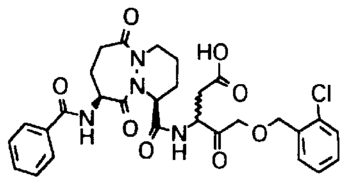 | 1046 | 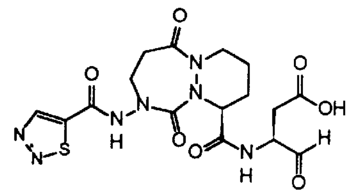 |
| 246 | 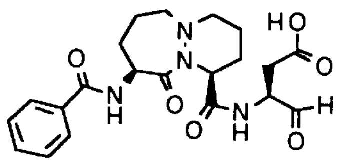 | 1047 | 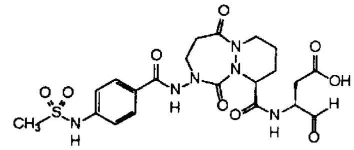 |
| 265 | 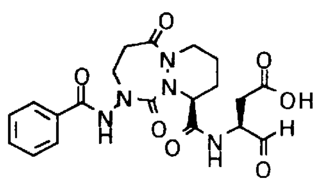 | 1048 | 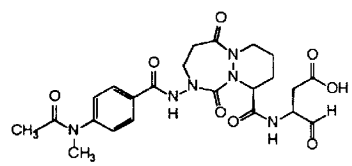 |
| 280 | 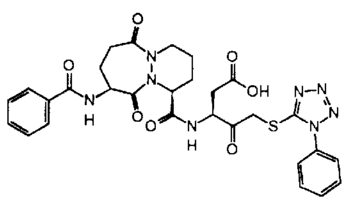 | 1049 | 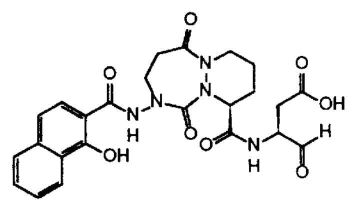 |
| 281 | 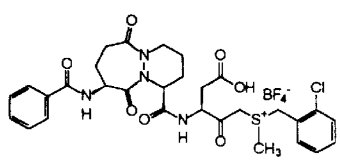 | 1050 | 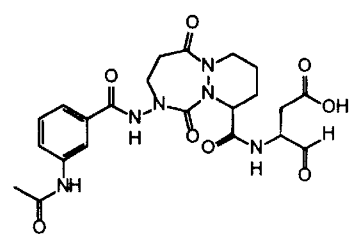 |

Figure 6

| Compound | Structure | Compound | Structure |
|---|---|---|---|
| 282 | 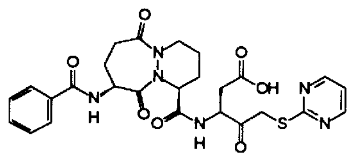 | 1051 | 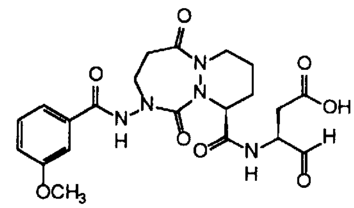 |
| 283 | 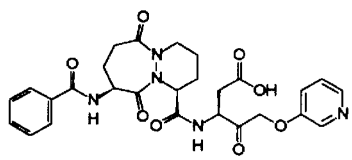 | 1052 | 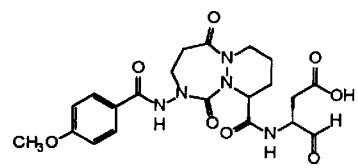 |
| 284 | 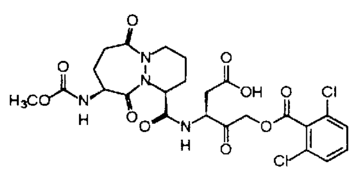 | 1053 | 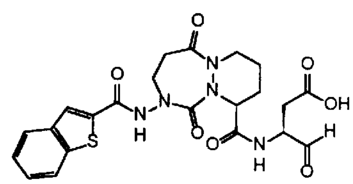 |
| 285 | 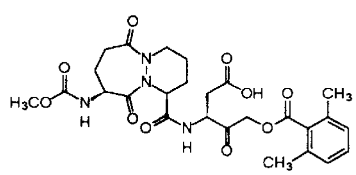 | 1054 | 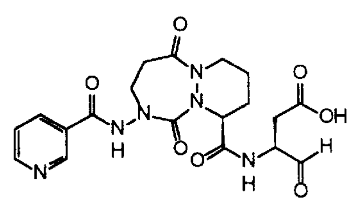 |
| 286 | 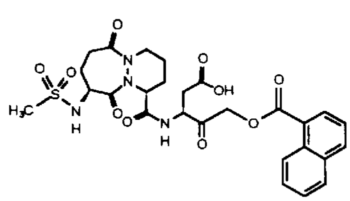 | 1055 | 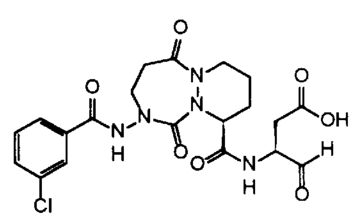 |

| Compound | Structure | Compound | Structure |
|---|---|---|---|
| 605e | 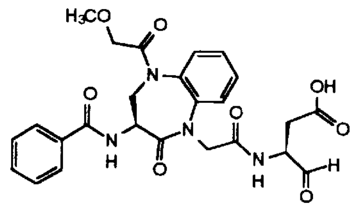 | 1067 | 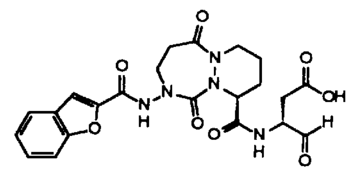 |
| 605f | 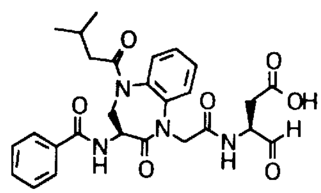 | 1068 | 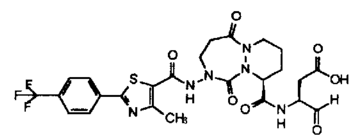 |
| 605g | 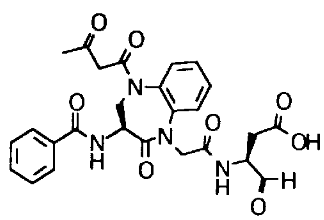 | 1069 | 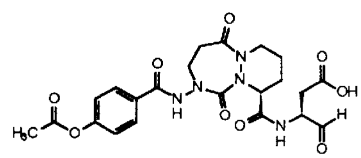 |
| 605h | 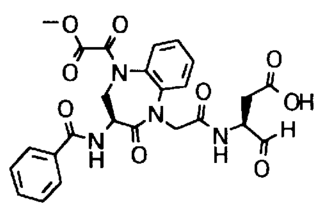 | 1070 | 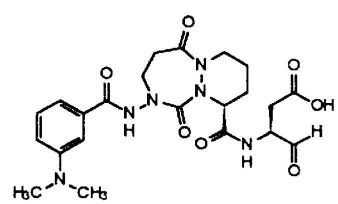 |
| 605i | 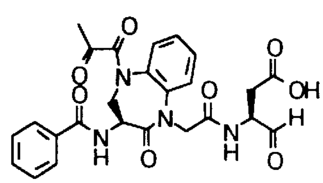 | 1071 | 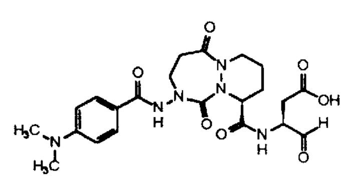 |

Figure 6
| Compound | Structure | Compound | Structure |
|---|---|---|---|
| 605j | 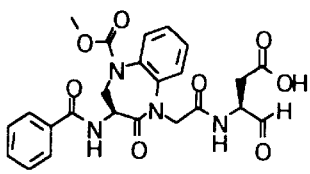 | 1073 | 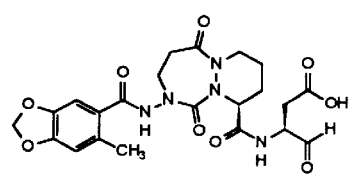 |
| 605m | 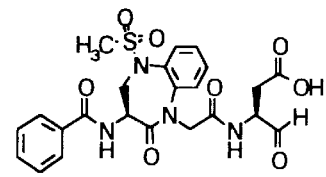 | 1074 | 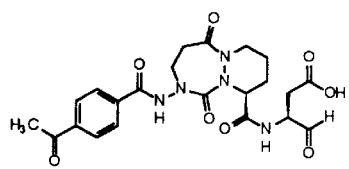 |
| 605n | 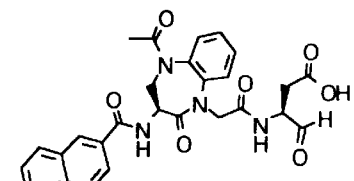 | 1075 | 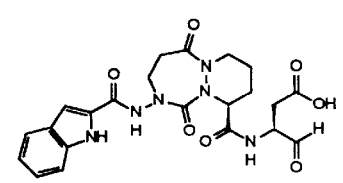 |
| 605o | 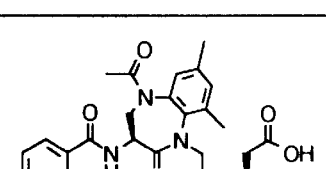 | 1076 | 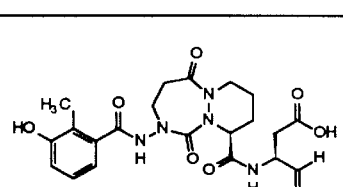 |
| 605p | 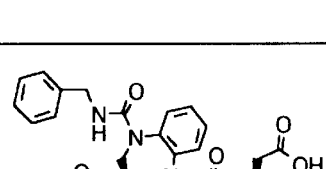 | 1077 | 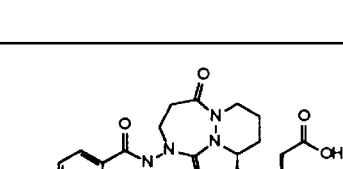 |

Figure 6

| Compound | Structure | Compound | Structure |
|---|---|---|---|
| 605q | 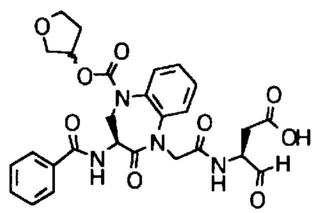 | 1078 | 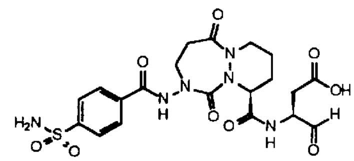 |
| 605s | 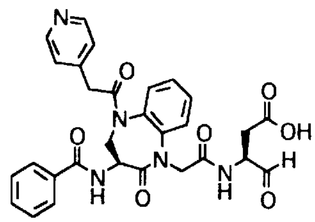 | 1079 | 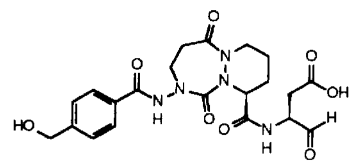 |
| 605t | 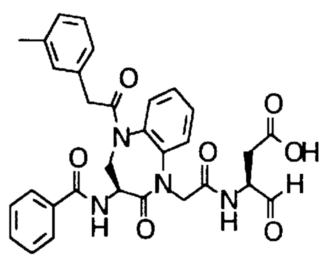 | 1080 | 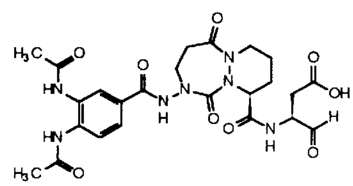 |
| 605v | 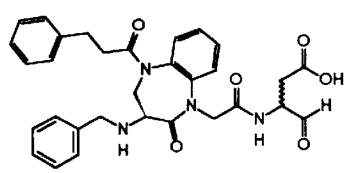 | 1081 | 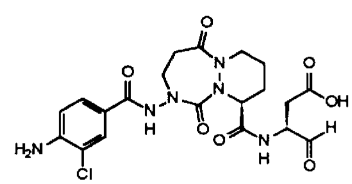 |
| 609a | 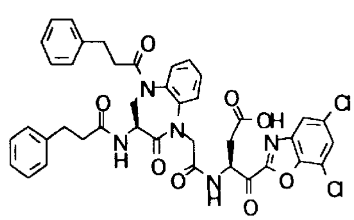 | 1081s | 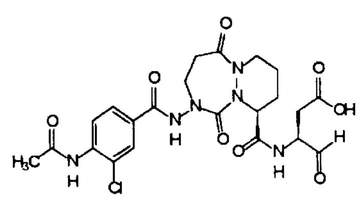 |

Figure 6
| Compound | Structure | Compound | Structure |
|---|---|---|---|
| 609b | 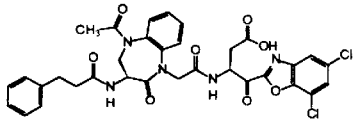 | 1082 | 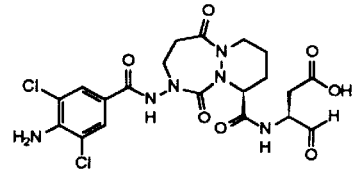 |
| 813e | 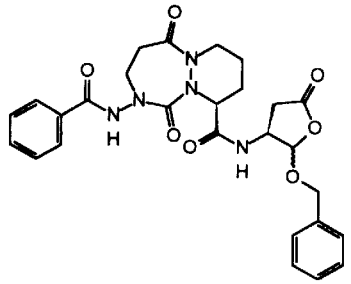 | 1082s | 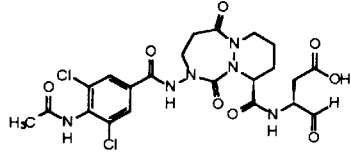 |
| 814c | 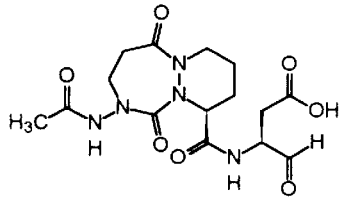 | 1083 | 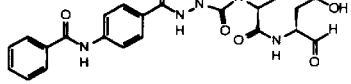 |
| 817c | 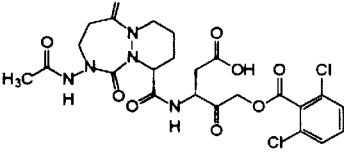 | 1084 | 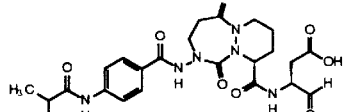 |
| 817d | 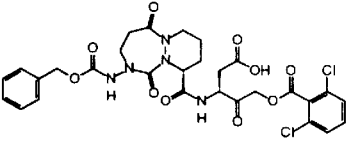 | 1085 | 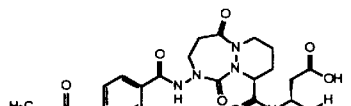 |
| 817e | 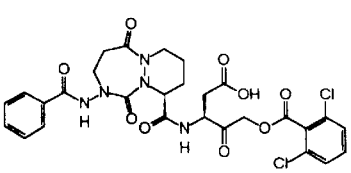 | 1086 | 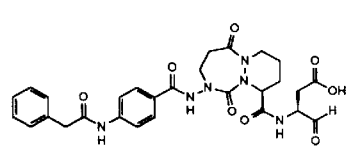 |

Figure 6

| Compound | Structure | Compound | Structure |
|---|---|---|---|
| 820b | 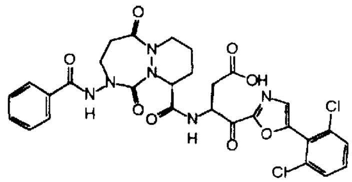 | 1087 | 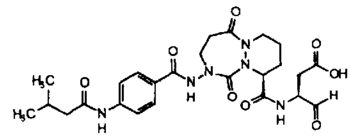 |
| 823b | 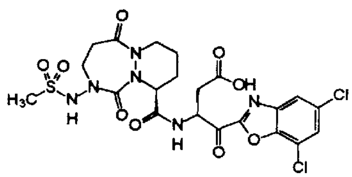 | 1088 | 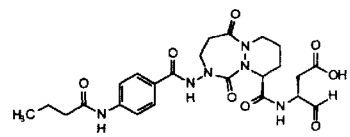 |
| 823e | 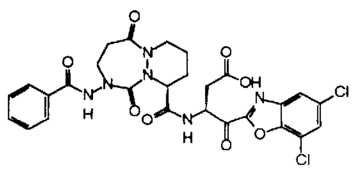 | 1089 | 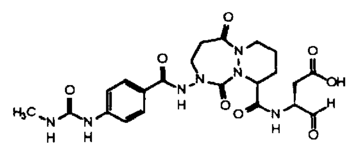 |
| 826e | 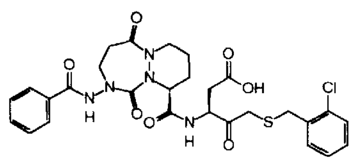 | 1090 | 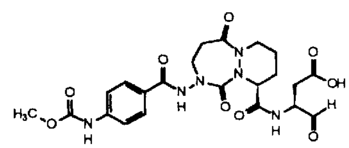 |
| 827e | 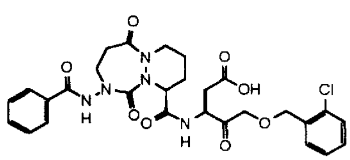 | 1091 | 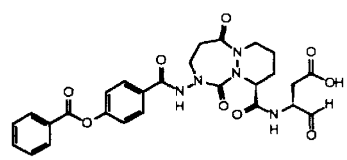 |
| 880 | 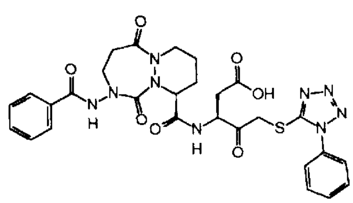 | 1093 | 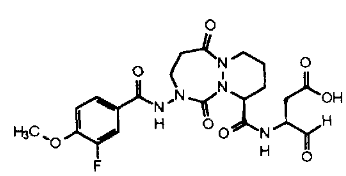 |

Figure 6

| Compound | Structure | Compound | Structure |
|---|---|---|---|
| 881 | 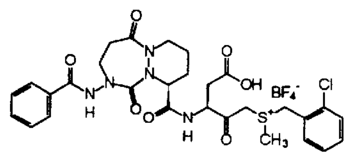 | 1094 | 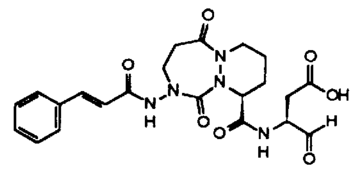 |
| 882 | 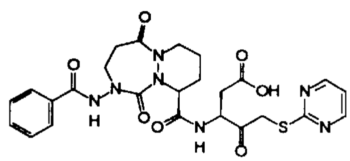 | 1095 | 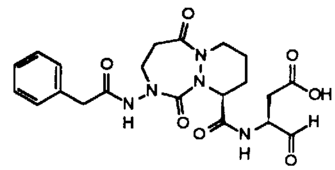 |
| 883 | 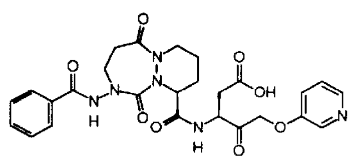 | 1096 | 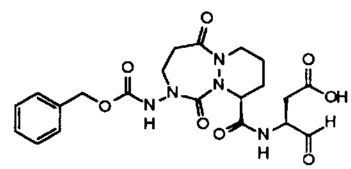 |
| 884 | 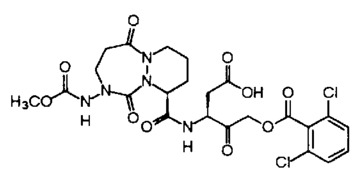 | 1097 | 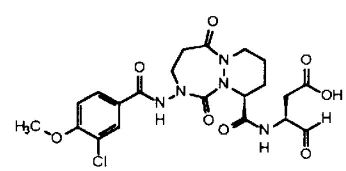 |
| 885 | 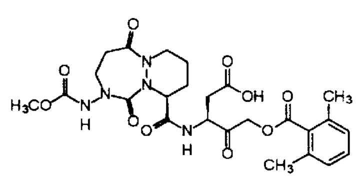 | 1098 | 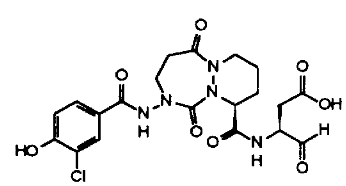 |

Figure 6

| Compound | Structure | Compound | Structure |
|---|---|---|---|
| 886 | 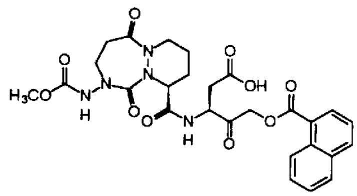 | 1099 | 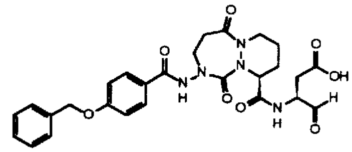 |
| 887 | 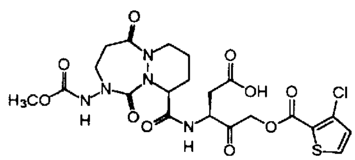 | 2001 | 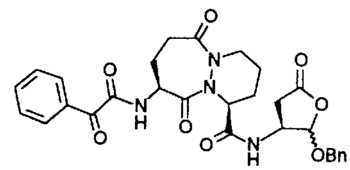 |
| 902 | 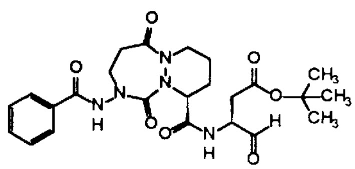 | 2002 | 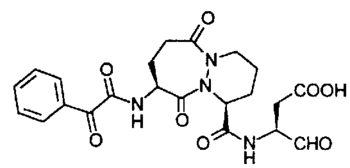 |
| 904a | 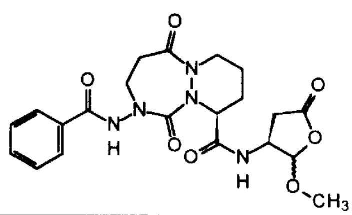 | 2100a | 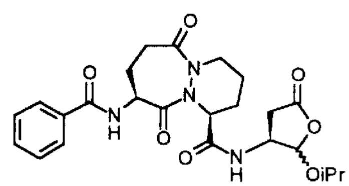 |
| 907a | 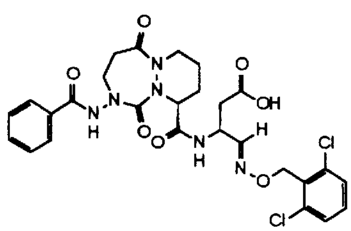 | 2100b | 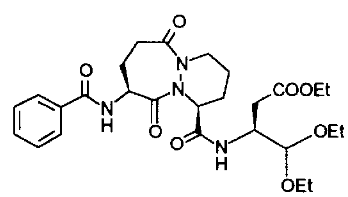 |
| 907b | 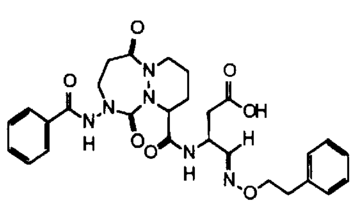 | 2100c | 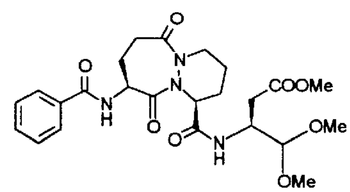 |

Figure 6

| Compound | Structure | Compound | Structure |
|---|---|---|---|
| 1004 | 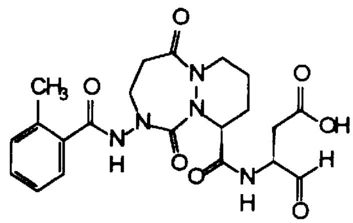 | 2100d | 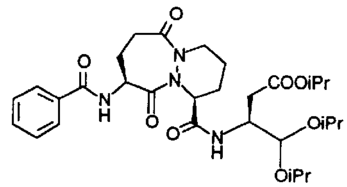 |
| 1005 | 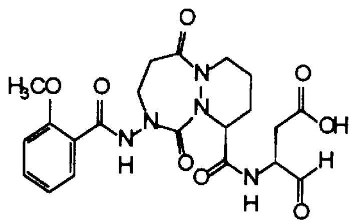 | 2100e | 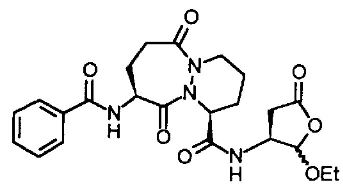 |
| 1006 | 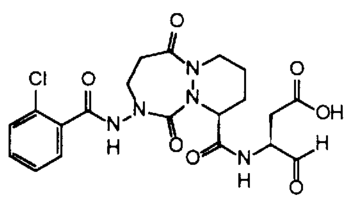 | 2201 | 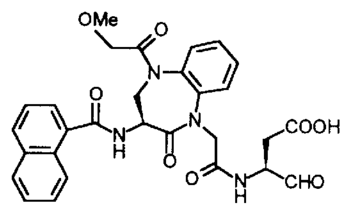 |
| 1007 | 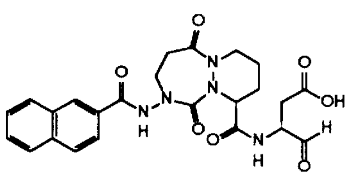 | 257 | 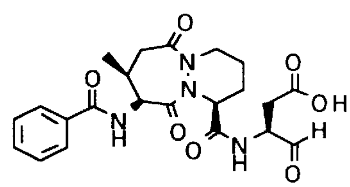 |
| 1008 | 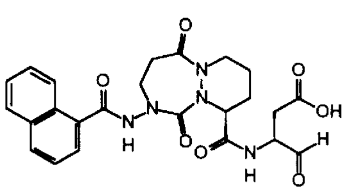 | 302 | 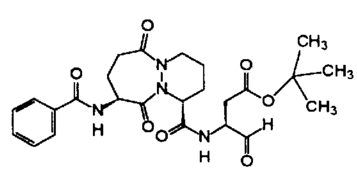 |

| Compound | Structure | Compound | Structure |
|---|---|---|---|
| 1035 | 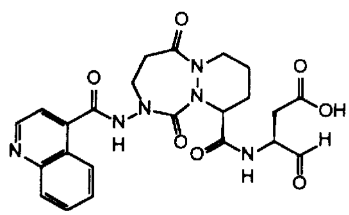 | | |

| Compound | Structure | Compound | Structure |
|---|---|---|---|
| 409 | 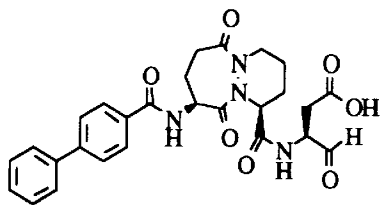 | 457 | 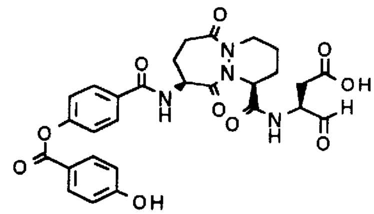 |
| 410 | 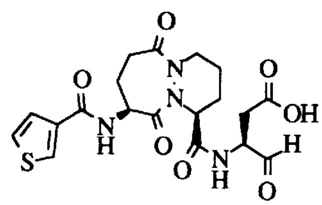 | 458 | 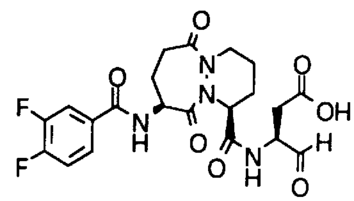 |
| 411 | 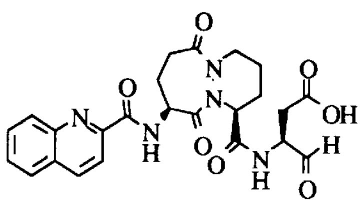 | 459 | 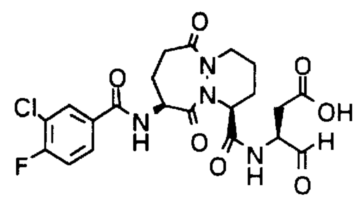 |
| 412 | 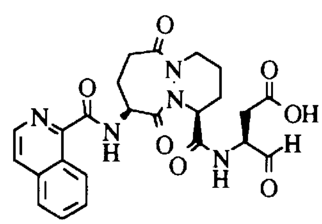 | 460 | 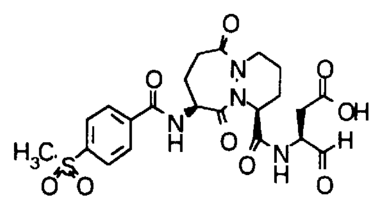 |
| 413 | 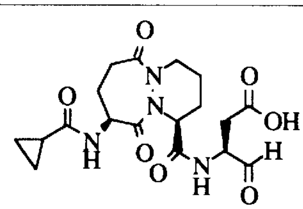 | 461 | 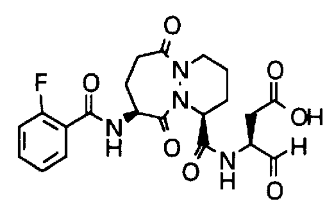 |
| 415 | 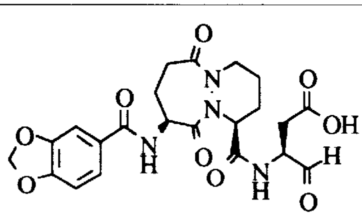 | 462 | 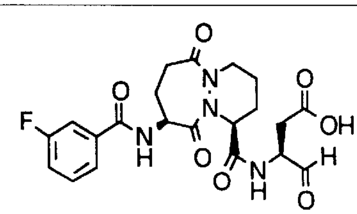 |

| Compound | Structure | Compound | Structure |
|---|---|---|---|
| 434 | 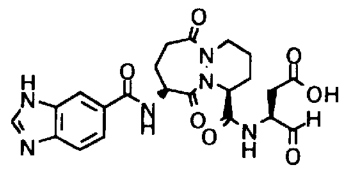 | 482 | 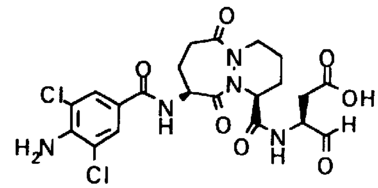 |
| 435 | 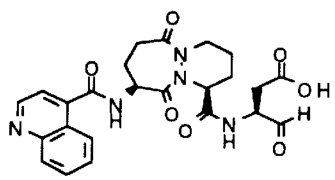 | 483 | 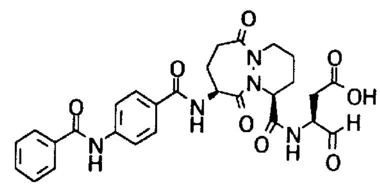 |
| 436 | 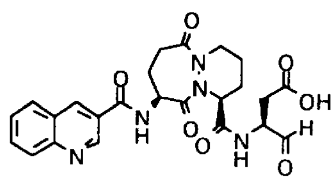 | 484 | 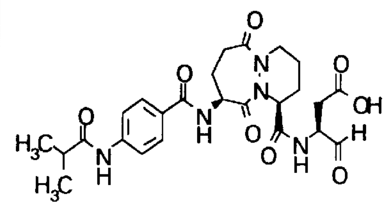 |
| 437 | 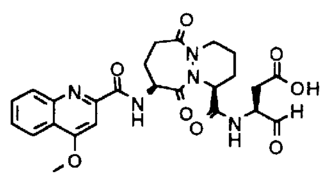 | 485 | 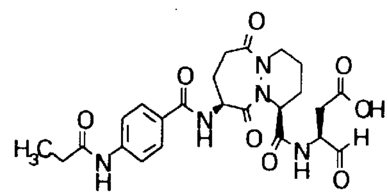 |
| 438 | 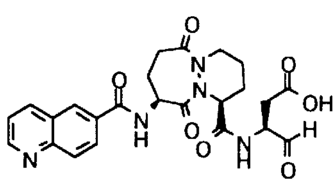 | 486 | 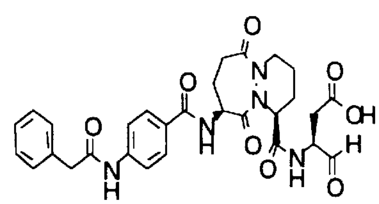 |
| 439 | 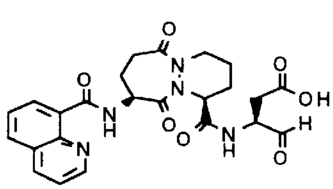 | 487 | 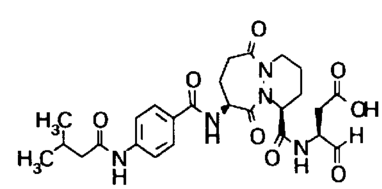 |

Figure 6

| Compound | Structure | Compound | Structure |
|---|---|---|---|
| 440 | 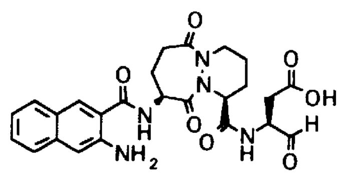 | 488 | 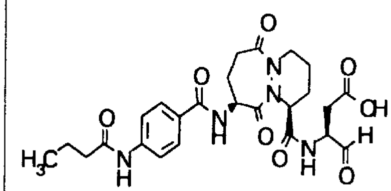 |
| 441 | 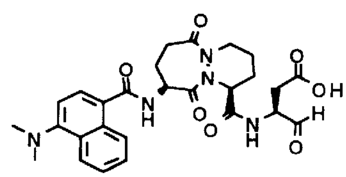 | 489 | 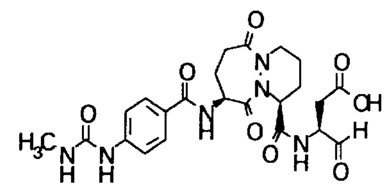 |
| 442 | 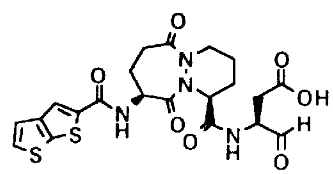 | 490 | 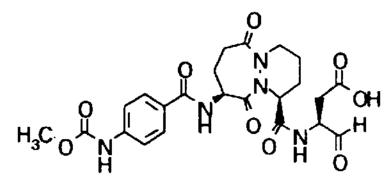 |
| 443 | 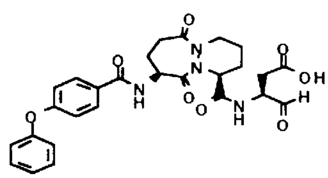 | 491 | 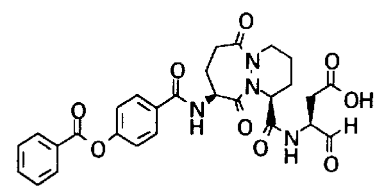 |
| 444 | 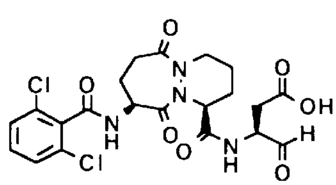 | 493 | 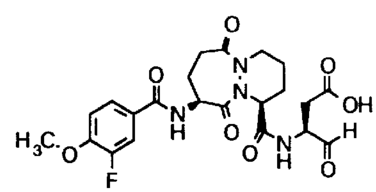 |
| 445 | 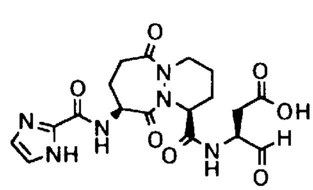 | 494 | 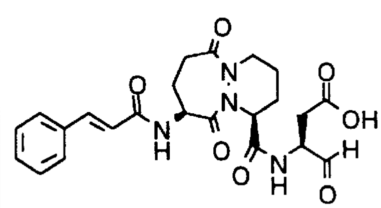 |

Figure 6

| Compound | Structure | Compound | Structure |
|---|---|---|---|
| 446 | 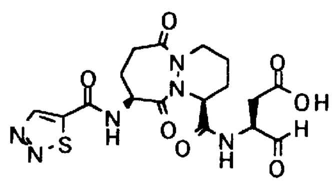 | 495 | 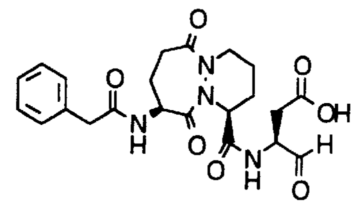 |
| 447 | 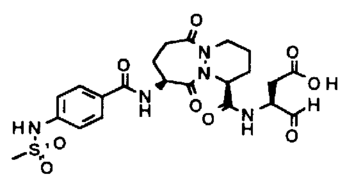 | 496 | 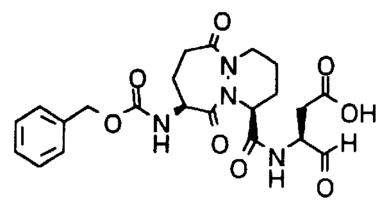 |
| 448 | 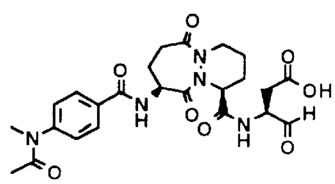 | 497 | 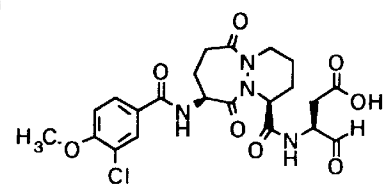 |
| 449 | 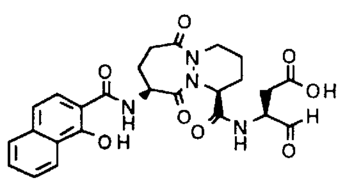 | 498 | 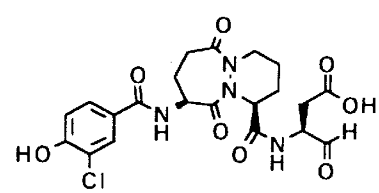 |
| 450 | 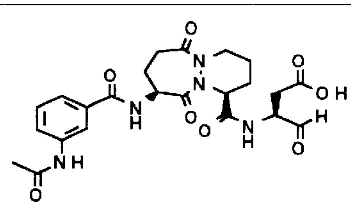 | 499 | 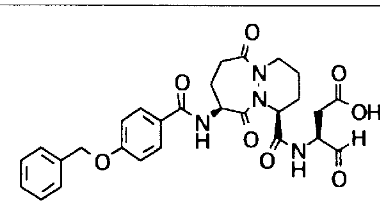 |

| Compound | Structure | Compound | Structure |
|---|---|---|---|
| 627 | 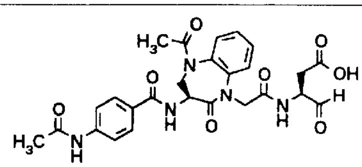 | | |

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (ix) FEATURE:
          (A) NAME/KEY: Modified-site
          (B) LOCATION: 1
          (D) OTHER INFORMATION: /note= "tyrosine is acetylated"

(ix) FEATURE:
          (A) NAME/KEY: Modified-site
          (B) LOCATION: 4
          (D) OTHER INFORMATION: /note= "aspartic acid carboxy
               terminus is reduced to an aldehyde"

(xi) SEQUENCE DESCRIPTION: SEQ ID NO:1:

Tyr Val Ala Asp
1

(2) INFORMATION FOR SEQ ID NO:2:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (ix) FEATURE:
          (A) NAME/KEY: Modified-site
          (B) LOCATION: 1
          (D) OTHER INFORMATION: /note= "aspartic acid is
               acetylated"

(ix) FEATURE:
          (A) NAME/KEY: Modified-site
          (B) LOCATION: 4
          (D) OTHER INFORMATION: /note= "aspartic acid carboxy
               terminus is reduced to an aldehyde"

(xi) SEQUENCE DESCRIPTION: SEQ ID NO:2:

Asp Glu Val Asp
1

(2) INFORMATION FOR SEQ ID NO:3:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:3:

Asn Phe Gly Arg Leu
1               5

(2) INFORMATION FOR SEQ ID NO:4:

(i) SEQUENCE CHARACTERISTICS:
           (A) LENGTH: 31 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "forward primer"

(iii) HYPOTHETICAL: NO (xi) SEQUENCE DESCRIPTION: SEQ ID NO:4:

GGAATTCCAT ATGGCTGCCA TGTCAGAAGA C                          31

(2) INFORMATION FOR SEQ ID NO:5:

(i) SEQUENCE CHARACTERISTICS:
           (A) LENGTH: 37 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (xi) SEQUENCE DESCRIPTION: SEQ ID NO:5:

GGTTAACCAT ATGCTAACTT TGATGTAAGT TAGTGAG                    37

(2) INFORMATION FOR SEQ ID NO:6:

(i) SEQUENCE CHARACTERISTICS:
           (A) LENGTH: 21 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:6:

Met Gly Ser Ser His His His His His His Ser Ser Gly Leu Val Pro
1               5                   10                  15

Arg Gly Ser His Met
            20

(2) INFORMATION FOR SEQ ID NO:7:

(i) SEQUENCE CHARACTERISTICS:
           (A) LENGTH: 6 amino acids
           (B) TYPE: amino acid
           (C) STRANDEDNESS: single
           (D) TOPOLOGY: linear (ii) MOLECULE TYPE: peptide (iii) HYPOTHETICAL: NO -continued

```
    (iv) ANTI-SENSE: NO (xi) SEQUENCE DESCRIPTION: SEQ ID NO:7:

Leu Val Pro Arg Gly Ser
1               5

(2) INFORMATION FOR SEQ ID NO:8:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 1
        (D) OTHER INFORMATION: /note= "tyrosine is succinylated"

(ix) FEATURE:
        (A) NAME/KEY: Modified-site
        (B) LOCATION: 4
        (D) OTHER INFORMATION: /note= "aspartic acid terminal
             carboxy group is derivatized as a p-nitroanilide
             derivative"

(xi) SEQUENCE DESCRIPTION: SEQ ID NO:8:

Tyr Val Ala Asp
1

(2) INFORMATION FOR SEQ ID NO:9:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 1
        (D) OTHER INFORMATION: /note= "tyrosine is acetylated"

(ix) FEATURE:
        (A) NAME/KEY: Modified-site
        (B) LOCATION: 4
        (D) OTHER INFORMATION: /note= "aspartic acid carboxy
             terminus is derivatized as an amino-4-methylco
             umarin derivative"

(xi) SEQUENCE DESCRIPTION: SEQ ID NO:9:

Tyr Val Ala Asp
```

COMPOSITIONS AND METHODS FOR DECREASING IGIF AND IFN-γ PRODUCTION BY ADMINISTERING AN ICE INHIBITOR

TECHNICAL FIELD OF THE INVENTION

The present invention relates to methods and pharmaceutical compositions for decreasing the production of interferon-gamma inducing factor (IGIF). The invention also relates to methods and pharmaceutical compositions for decreasing the production of interferon-gamma (IFN-γ). The compositions comprise a therapeutically effective amount of a compound which inhibits interleukin-1β converting enzyme (ICE) and a pharmaceutically acceptable carrier. The methods comprise the step of administering the above compositions to a subject. The present invention also relates to methods for treating or reducing the advancement, severity or effects of an IGIF- or IFN-γ-mediated inflammatory, infectious or autoimmune condition.

BACKGROUND OF THE INVENTION

Interferon-gamma inducing factor (IGIF) is an approximately 18-kDa polypeptide that stimulates T-cell production of interferon-gamma (IFN-γ). IGIF is produced by activated Kupffer cells and macrophages in vivo and is exported out of such cells upon endotoxin stimulation. Thus, a compound that decreases IGIF production would be useful as an inhibitor of such T-cell stimulation which in turn would reduce the levels of IFN-γ production by those cells.

IFN-γ is a cytokine with immunomodulatory effects on a variety of immune cells. In particular, IFN-γ is involved in macrophage activation and Th1 cell selection (F. Belardelli, APMIS, 103, p. 161 (1995)). IFN-γ exerts its effects in part by modulating the expression of genes through the STAT and IRF pathways (C. Schindler and J. E. Darnell, Ann. Rev. Biochem., 64, p. 621 (1995); T. Taniguchi, J. Cancer Res. Clin. Oncol., 121, p. 516 (1995)).

Mice lacking IFN-γ or its receptor have multiple defects in immune cell function and are resistant to endotoxic shock (S. Huang et al., Science, 259, p. 1742 (1993); D. Dalton et al., Science, 259, p. 1739 (1993); B. D. Car et al., J. Exp. Md., 179, p. 1437 (1994)). Along with IL-12, IGIF appears to be a potent inducer of IFN-γ production by T cells (H. Okamura et al., Infection and Immunity, 63, p. 3966 (1995); H. Okamura et al., Nature, 378, p. 88 (1995); S. Ushio et al., J. Immunol., 156, p. 4274 (1996)).

IFN-γ has been shown to contribute to the pathology associated with a variety of inflammatory, infectious and autoimmune disorders and diseases. Thus, compounds capable of decreasing IFN-γ production would be useful to ameliorate the effects of IFN-γ related pathologies.

The biological regulation of IGIF and thus IFN-γ has not been elucidated. It is known that IGIF is synthesized as a precursor protein, called "pro-IGIF". It has been unclear, however, how pro-IGIF is cleaved and whether its processing has biological importance.

Accordingly, compositions and methods capable of regulating the conversion of pro-IGIF to IGIF would be useful for decreasing IGIF and IFN-γ production in vivo, and thus for ameliorating the detrimental effects of these proteins which contribute to human disorders and diseases.

Another cytokine, IL-1β, is produced as an inactive precursor (pre-IL-1β) which is proteolytically cleaved into an active, mature form (IL-1β) by a cysteine protease called interleukin-1β converting enzyme (ICE). ICE is a member of a larger family of cysteine proteases, called the ICE/CED-3 family, which share common structural and functional features. See, e.g., P. A. Henkarp, Immunity, 4, p. 195 (1996); D. W. Nicholson, Nature Biotechnology, 14, p. 297 (1996).

However, ICE and other members of the ICE/CED-3 family have not previously been linked to the conversion of pro-IGIF to IGIF or to IFN-γ production in vivo.

SUMMARY OF THE INVENTION

The present invention solves the problems above by providing methods and pharmaceutical compositions for decreasing the production of interferon-gamma inducing factor (IGIF) in vivo. The invention also provides methods and pharmaceutical compositions for decreasing the production of interferon-gamma (IFN-γ) in vivo. The compositions of this invention comprise a therapeutically effective amount of a compound which inhibits interleukin-1β converting enzyme (ICE) and a pharmaceutically acceptable carrier. The methods of this invention comprise the step of administering one or more of the above compositions to a subject. The present invention also provides methods for treating or reducing the advancement, severity or effects of an IGIF- or IFN-γ-mediated inflammatory, infectious or autoimmune condition.

BRIEF DESCRIPTION OF THE FIGURES

FIG. 3A Kupffer cells from mice lacking ICE are defective in the export of IGIF. Kupffer cells from wild type mice (ICE+/+) or ICE-deficient mice homozygous for an ICE mutation (ICE−/−) were isolated and primed with LPS for three hours. The levels of immunoreactive IGIF polypeptides in the conditioned media (ng/ml) of wild type cells were measured by ELISA (Example 3). N.D. (not detectable) indicates that the IGIF concentration was less than 0.1 ng/ml.

FIG. 3B Kupffer cells from mice lacking ICE are defective in the export of mature IGIF. Kupffer cells from wild type mice (ICE+/+) or ICE deficient mice homozygous for an ICE mutation (ICE−/−) were isolated and primed with LPS for three hours. Primed cells were metabolically labeled with $^{35}$S-methionine, proteins from cell lysates and conditioned medium immunoprecipitated with anti-IGIF antisera and separated by SDS-PAGE (Example 3). Mobilities of pro-IGIF and the 18-kDa mature IGIF are indicated on the right. Molecular mass markers in kDa are shown on the left.

FIG. 3C Serum from ICE-deficient mice contains reduced levels of IGIF. Serum samples from wild type mice (ICE+/+) or ICE deficient mice homozygous for an ICE mutation (ICE−/−) were assayed for IGIF levels (ng/ml) by ELISA (Example 3).

FIG. 3D Serum from ICE-deficient mice contains reduced levels of IFN-γ. Serum samples from wild type mice (ICE+/+) or ICE deficient mice homozygous for an ICE mutation (ICE−/−) were assayed for IFN-γ levels (ng/ml) by ELISA (Example 3).

FIG. 6 Structures of selected ICE inhibitors.

DETAILED DESCRIPTION OF THE INVENTION

In order that the invention described herein may be more fully understood, the following detailed description is set forth.

The following abbreviations and definitions are used throughout the application.

The term "interferon gamma inducing factor" or "IGIF" refers to a factor which is capable of stimulating the endogenous production of IFN-γ.

The term "ICE inhibitor" refers to a compound which is capable of inhibiting the ICE enzyme. ICE inhibition may be determined using the methods described and incorporated by reference herein. The skilled practitioner realizes that an in vivo ICE inhibitor is not necessarily an in vitro ICE inhibitor. For example, a prodrug form of a compound typically demonstrates little or no activity in in vitro assays. Such prodrug forms may be altered by metabolic or other biochemical processes in the patient to provide an in vivo ICE inhibitor.

The term "cytokine" refers to a molecule which mediates interactions between cells.

The term "condition" refers to any disease, disorder or effect that produces deleterious biological consequences in a subject.

The term "subject" refers to an animal, or to one or more cells derived from an animal. Preferably, the animal is a mammal, most preferably a human. Cells may be in any form, including but not limited to cells retained in tissue, cell clusters, immortalized cells, transfected or transformed cells, and cells derived from an animal that have been physically or phenotypically altered.

The term "patient" refers to a subject which is a human.

Other definitions are set forth in the specification where necessary.

ICE and TX Cleave and Thereby Activate Pro-IGIF

The ICE protease was identified previously by virtue of its ability to process inactive pro-IL-1β to mature active IL-1β, a pro-inflammatory molecule, in vitro and in vivo. Here we show that ICE and its close homologue TX (Caspase-4, C. Faucheu et al., *EMBO*, 14, p. 1914 (1995)) can proteolytically cleave inactive pro-IGIF. This processing step is required to convert pro-IGIF to its active mature form, IGIF. Cleavage of pro-IGIF by ICE, and presumably by TX, also facilitates the export of IGIF out of cells.

Figure 1A:
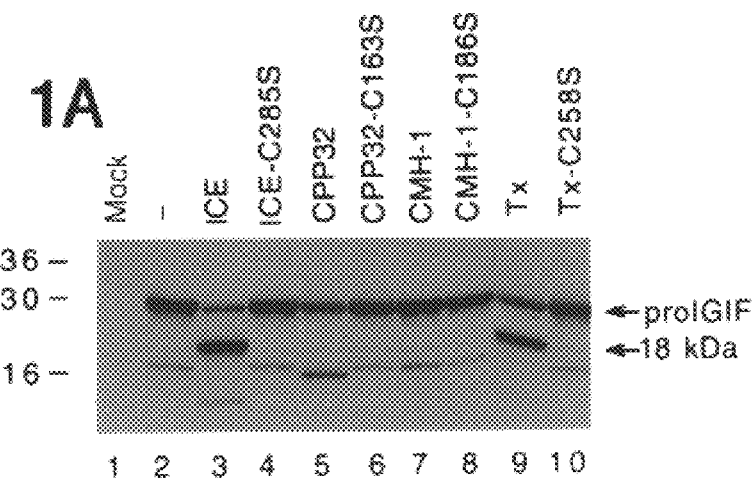
FIG. 1A ICE cleaves pro-IGIF in vivo. Cell lysates from Cos cells transfected with the various indicated expression plasmids or controls were analyzed for the presence of IGIF by separating proteins by SDS-PAGE and immunoblotting with anti-IGIF antisera. Mobilities of pro-IGIF and the 18-kDa mature IGIF are indicated on the right. Molecular weight markers in kDa are shown on the left (Example 1).

We first used transient co-expression of plasmids transfected into Cos cells to determine whether any known members of the ICE/CED-3 protease family can process pro-IGIF to IGIF in cultured cells (Example 1) (FIG. 1A).

FIG. 1A demonstrates that ICE cleaves pro-IGIF in Cos cells co-transfected with plasmids that express pro-IGIF in the presence of active ICE. Cos cells were transfected with an expression plasmid for pro-IGIF alone (lane 2) or in combination with the indicated expression plasmids encoding wild type or inactive mutants of ICE/CED-3 family of proteases (lanes 3–12). Cell lysates were prepared and analyzed for the presence of IGIF protein by immunoblotting with an anti-IGIF antiserum. Lane 1 contained lysates from mock transfected cells.

Co-expression of pro-IGIF with ICE or TX resulted in the cleavage of pro-IGIF into a polypeptide similar in size to the naturally-occurring 18-kDa mature IGIF. This processing event is blocked by single point mutations that alter the catalytic cysteine residues and thus inactivate ICE and TX (Y. Gu et al., *EMBO*, 14, p. 1923 (1995)).

Co-expression with CPP32 (Caspase-3), a protease involved in programmed cell death (T. Fernandes-Alnemri et al., *J. Biol. Chem.*, 269, p. 30761 (1994); D. W. Nicholson et al., *Nature*, 376 p. 37 (1995)), resulted in the cleavage of pro-IGIF into a smaller polypeptide, while co-expression with CMH-1 (Caspase-7), a close homolog of CPP32 (J. A. Lippke et al., *J. Biol. Chem.*, 271, p. 1825 (1996)), failed to cleave pro-IGIF to any significant extent. Thus, ICE and TX appear to be capable of cleaving pro-IGIF into a polypeptide similar in size to the naturally-occurring 18 kDa IGIF.

We next examined the ability of these cysteine proteases to cleave pro-IGIF in vitro using a purified, recombinant (His)$_6$-tagged pro-IGIF as a substrate (Example 1).

Figure 1B:
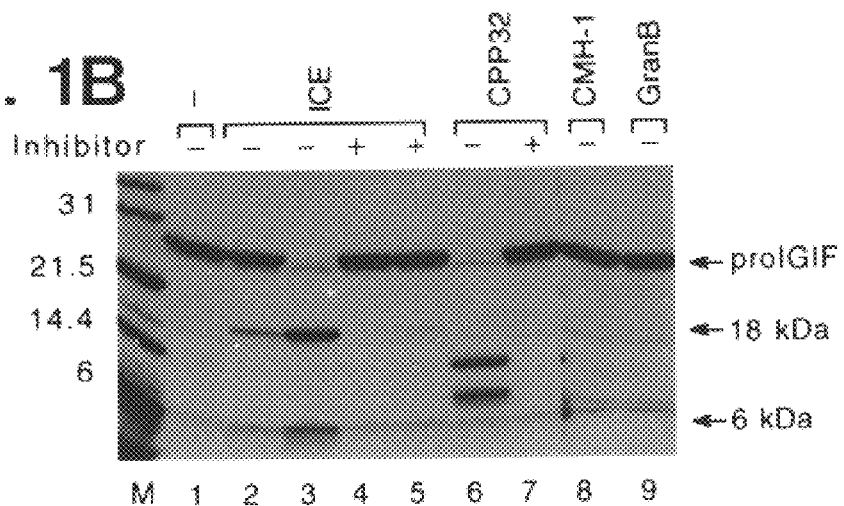
FIG. 1B ICE cleaves pro-IGIF at the authentic processing site in vitro as shown by Coomassie blue staining of proteolytic reaction products separated by SDS-PAGE (Example 1).

FIG. 1B demonstrates that pro-IGIF is cleaved in vitro by ICE. Purified recombinant (His)$_6$-tagged pro-IGIF (2 μg)

was incubated with the indicated cysteine protease in the presence or absence of ICE or CPP32 inhibitors as described in Example 1. The cleavage products were analyzed by SDS-PAGE and Coomassie Blue staining. The proteases and inhibitors used were: lane 1, buffer control; lane 2, 0.1 nM ICE; lane 3, 1 nM ICE; lanes 4 and 5, 1 nM ICE with 10 nM Cbz-Val-Ala-Asp-[(2,6dichlorobenzoyl)oxy]methyl ketone and 100 nM Ac-Tyr-Val-Ala-Asp-aldehyde, respectively; lanes 6 and 7, 15 nM CPP32 with and without 400 nM Ac-Asp-Glu-Val-Asp-aldehyde (SEQ ID No. 2) (D. W. Nicholson et al., Nature, 376, p. 37 (1995)), respectively; lane 8, 100 nM CMH-1; lane 9, 10 units/ml granzyme B; and M, molecular weight markers in kDa.

ICE cleaved the 24 kDa pro-IGIF into two polypeptides of approximately 18-kDa and 6-KDa. N-terminal amino acid sequencing of the ICE cleavage products indicated that the 18-kDa polypeptide contains the same N-terminal amino acid residues (Asn-Phe-Gly-Arg-Leu) (SEQ ID No. 3) as the naturally occurring IGIF. This shows that ICE cleaves pro-IGIF at the authentic processing site (Asp35-Asn36) (H. Okamura et al., Infection and Immunity, 63, p. 3966 (1995); H. Okamura et al., Nature, 378, p. 88 (1995)). N-terminal amino acid sequencing of the CPP32 cleavage products indicated that CPP32 cleaved pro-IGIF at Asp69-Ile70.

The cleavage by ICE of pro-IGIF is highly specific with a catalytic efficiency ($k_{cat}/K_M$) of $1.4 \times 10^7$ $M^{-1}$ $s^{-1}$ ($K_M$=0.6±0.1 $\mu$M; $k_{cat}$=8.6±0.3 $s^{-1}$) and is inhibited by specific ICE inhibitors (Ac-Tyr-Val-Ala-Asp-aldehyde, and Cbz-Val-Ala-Asp-[(2,6-(dichlorobenzoyl)oxy]methylketone, (N. A. Thornberry et al., Nature, 356, p. 768 (1992); R. E. Dolle et al., J. Med. Chem., 37, p. 563 (1994)).

Figure 1C:
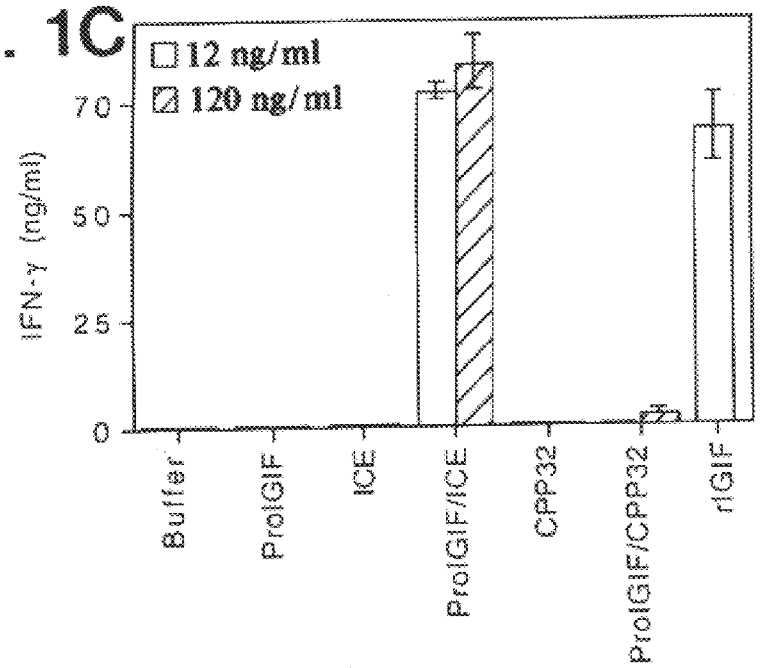
FIG. 1C ICE cleavage converts inactive pro-IGIF to active IGIF which induces IFN-γ production in Th1 helper cells. Uncleaved (Pro-IGIF), ICE-cleaved (Pro-IGIF/ICE), CPP32-cleaved (Pro-IGIF/CPP32), and recombinant mature IGIF (rIGIF) were incubated with A.E7 Th1 cells at 12 ng/ml and 120 ng/ml for eighteen hours and the levels of IFN-γ released into the culture medium assayed by ELISA (Example 1). A.E7 cells cultured with buffer, ICE alone (ICE) or CPP32 alone (CPP32) were assayed similarly for negative controls. The numbers represent the average of three determinations.

FIG. 1C demonstrates that ICE cleavage in vitro activates pro-IGIF. Uncleaved pro-IGIF, ICE- or CPP32-cleaved products of pro-IGIF, or recombinant mature IGIF (rIGIF) were each added to A.E7 cell cultures to a final concentration of 12 ng/ml (open bar) or 120 ng/ml (hatched bar) (Example 1). Eighteen hours later, IFN-γ in the cultural medium was quantified by ELISA. While the uncleaved pro-IGIF had no detectable IFN-γ inducing activity, ICE-cleaved pro-IGIF was active in inducing IFN-γ production in Th1 cells.

Like ICE, the ICE homolog TX also cleaved pro-IGIF into similarly sized polypeptides. However, its catalytic efficiency was about two orders of magnitude lower than that shown for ICE.

Consistent with the observations from the Cos cell experiments above, CPP32 cleaved pro-IGIF at a different site (Asp69-Ile70) and the resulting polypeptides had little IFN-γ inducing activity (FIG. 1C). CMH-1 and granzyme B each failed to cleave pro-IGIF to any significant extent.

Together, these results demonstrate that, both in Cos cells and in vitro, ICE and TX are capable of processing the inactive pro-IGIF precursor at the authentic maturation site to generate a biologically active IGIF molecule.

Processing of Pro-IGIF by ICE Facilitates Its Export

IGIF is produced by activated Kupffer cells and macrophages in vivo and is exported out of the cells upon stimulation by endotoxin (H. Okamura et al., Infection and Immunity, 63, p. 3966 (1995); H. Okamura et al., Nature, 378, p. 88 (1995). We used the Cos cell co-expression system (Example 1) to examine whether the intracellular cleavage of pro-IGIF by ICE would facilitate the export of mature IGIF from the cell. Such is the case for pro-IL-1β when it is cleaved by ICE into active IL-1β (N. A. Thornberry et al., Nature, 356, p. 768 (1992)).

Figure 2A:
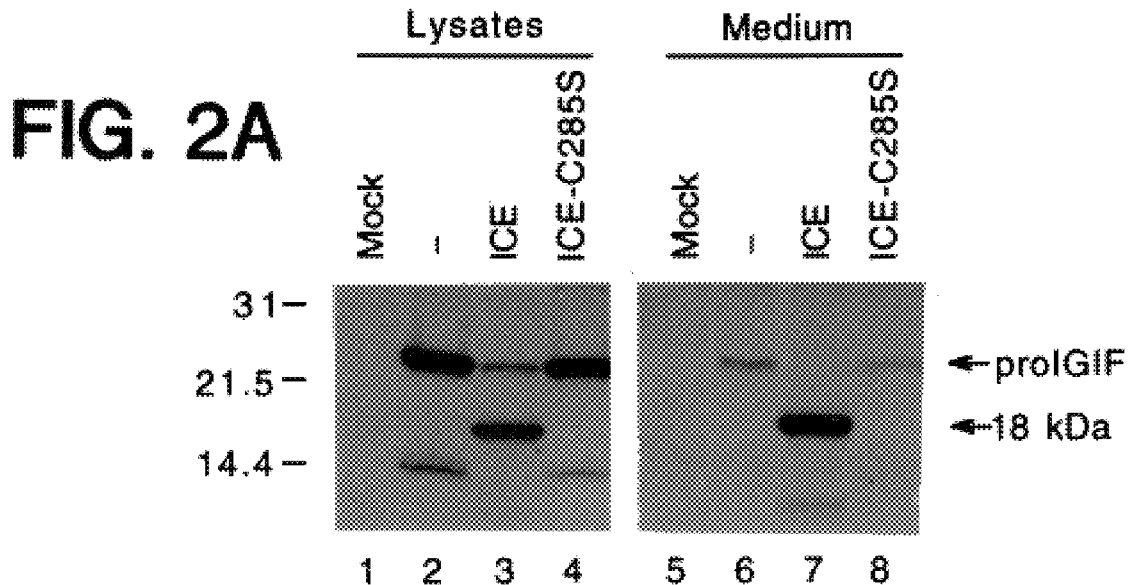
FIG. 2A Mature IGIF (18-kDa) is produced by Cos cells co-transfected with pro-IGIF and ICE-expressing plasmids. Cell lysates (left) and conditioned medium (right) from Cos cells transfected with a pro-IGIF expression plasmid in the absence (−) or presence of an expression plasmid encoding wild type (ICE) or inactive mutant (ICE-C285S) ICE. Transfected cells were metabolically labeled with $^{35}$S-methionine, proteins from cell lysates and conditioned medium immunoprecipitated with anti-IGIF antisera and separated by SDS-PAGE (Example 2). Mobilities of pro-IGIF and the 18-kDa mature IGIF are indicated on the right. Molecular weight markers in kDa are shown on the left.

In FIG. 2A, Cos cells transfected with an expression plasmid for pro-IGIF alone (lanes 2 and 6) or in combination with an expression plasmid encoding wild type (lanes 3 and 7) or inactive mutant ICE (lanes 4 and 8) were metabolically labeled with $^{35}$S-methionine (Example 2). Cell lysates (left) and conditioned medium (right) were immunoprecipitated with an anti-IGIF antiserum. The immunoprecipitated proteins were analyzed by SDS-PAGE and fluorography (FIG. 2A).

An 18 kDa polypeptide corresponding in size to mature IGIF was detected in the conditioned medium of Cos cells co-expressing pro-IGIF and ICE, while Cos cells co-expressing pro-IGIF and an inactive ICE mutant (ICE-C285S), or pro-IGIF alone (−) exported only very low levels of pro-IGIF and no detectable mature IGIF. We estimate that about 10% of the mature IGIF was exported from co-transfected cells, while greater than 99% of pro-IGIF was retained within the cells.

Figure 2B:
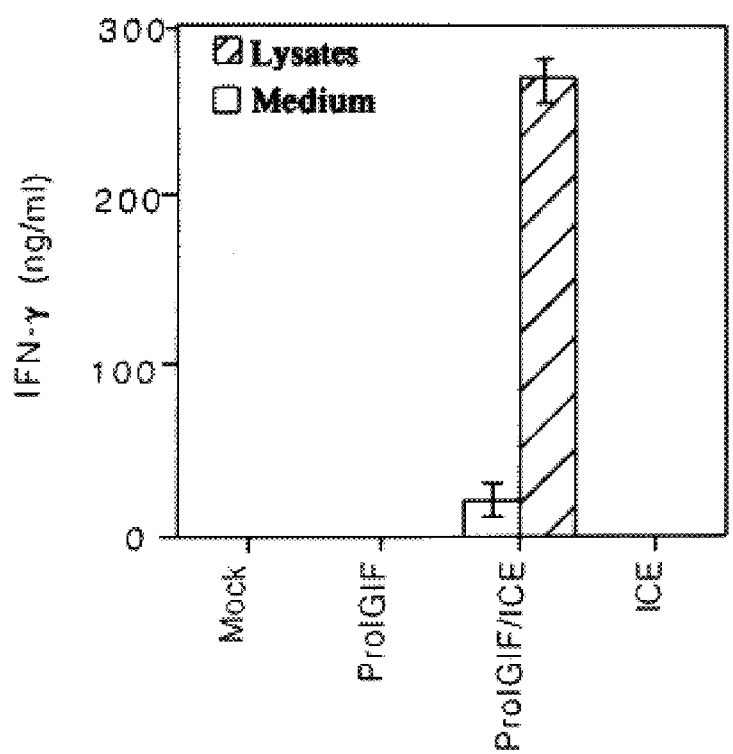
FIG. 2B IFN-γ inducing activity is detected in Cos cells co-transfected with pro-IGIF and ICE-expressing plasmids. Cell lysates (hatched bar) and conditioned medium (open bar) from Cos cells transfected with a pro-IGIF expression plasmid in the absence (Pro-IGIF) or presence (Pro-IGIF/ICE) of an expression plasmid encoding wild type (ICE) were assayed for IFN-γ levels (ng/ml) by ELISA. Cos cells transfected with buffer (Mock) or an ICE-expressing plasmid alone (ICE) served as negative controls (Example 2).

We also measured the presence of IFN-γ inducing activity in cell lysates and in the conditioned medium of the above transfected cells (Example 2). IFN-γ inducing activity was detected in both cell lysates and the conditioned medium of Cos cells co-expressing pro-IGIF and ICE, but not in cells expressing either pro-IGIF or ICE alone (FIG. 2B).

These results indicate that ICE cleavage of pro-IGIF facilitates the export of mature, active IGIF from cells.

Pro-IGIF is a Physioloaical Substrate of ICE In Vivo

To study the role of ICE in the proteolytic activation and export of IGIF under physiological conditions, we examined the processing of pro-IGIF and export of mature IGIF from lipopolysaccharide (LPS)-activated Kupffer cells harvested from Propiobacterium acnes-elicited wild type and ICE deficient (ICE−/−) mice (Example 3).

As shown in FIG. 3A, Kupffer cells from ICE−/− mice are defective in the export of IGIF. Kupffer cell lysates of wild type and ICE−/− mice contained similar amounts of IGIF as determined by ELISA. IGIF, however, could be detected only in the conditioned medium of wild type but not of the ICE−/− cells. Thus, ICE-deficient (ICE−/−) mice synthesize pro-IGIF, but fail to export it as extracellular pro- or mature IGIF.

To determine whether ICE-deficient (ICE−/−) mice process intracellular pro-IGIF but fail to export IGIF, Kupffer cells from wild type and ICE−/− mice were metabolically labeled with $^{35}$S-methionine and IGIF immunoprecipitation experiments were performed on cell lysates and conditioned media as described in Example 3. These experiments demonstrated that unprocessed pro-IGIF was present in both wild type and ICE−/− Kupffer cells. However, the 18 kDa mature IGIF was present only in the conditioned medium of wild type and not ICE−/− Kupffer cells (FIG. 3B). This shows that active ICE is required in cells for the export of processed IGIF out of the cell.

In addition, conditioned medium from wild type but not from ICE−/− Kupffer cells contained IFN-γ inducing activity that was not attributed to the action of IL-12 because it was insensitive to a neutralizing anti-IL-12 antibody. The absence of IGIF in the conditioned medium of ICE−/− Kupffer cells is consistent with the finding in Cos cells that the processing of pro-IGIF by ICE is required for the export of active IGIF.

FIGS. 3C and 3D show that, in vivo, ICE−/− mice have reduced serum levels of IGIF and IFN-γ, respectively. Wild type (ICE+/+) and ICE−/− mice (n=3) primed with heat-inactivated P. acnes were challenged with LPS (Example 4), and the levels of IGIF (FIG. 3C) and IFN-γ (FIG. 3D) in the sera of challenged mice were measured by ELISA three hours after LPS challenge (Example 3).

The sera of ICE−/− mice stimulated by P. acnes and LPS contained reduced levels of IGIF (FIG. 3C) and no detectable IFN-γ inducing activity in the presence of an anti-IL-12 antibody. The reduced serum levels of IGIF likely accounts for the significantly lower levels of IFN-γ in the hera of ICE-/- mice (FIG. 3D), because we have observed no significant difference in the production of IL-12 in ICE-/- mice under these conditions. Consistent with this interpretation is the finding that non-adherent splenocytes from wild type and ICE-/- mice produced similar amounts of IFN-γ when stimulated with recombinant active IGIF in vitro. Thus the impaired production of IFN-γ is not due to any apparent defect in the T cells of the ICE-/- mice.

Taken together, these results establish a critical role for ICE in processing the IGIF precursor and in the export of active IGIF both in vitro and in vivo.

Figure 4:
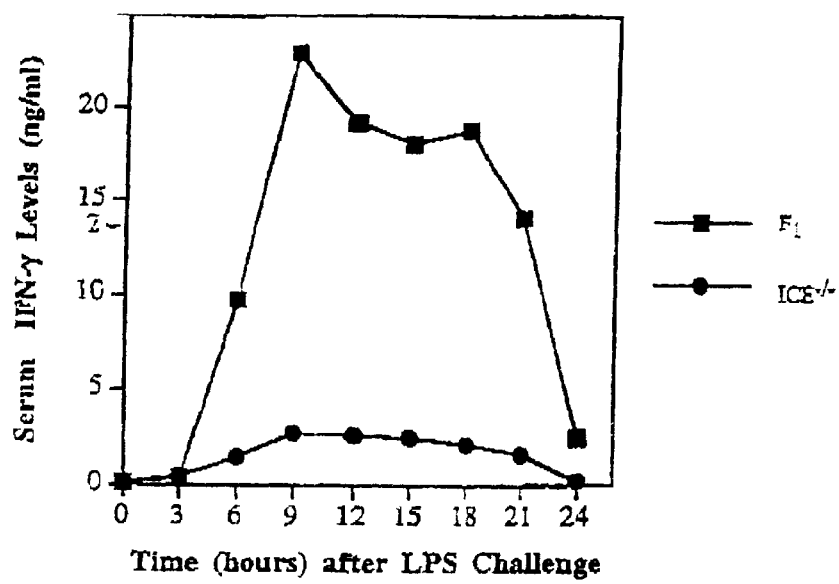
FIG. 4 Serum IFN-γ levels are significantly reduced in ICE-deficient mice after an acute challenge with LPS (Example 4). Serum samples from wild type mice (filled squares) or ICE-deficient mice (filled circles) were assayed for IFN-γ levels (ng/ml) by ELISA as a function of time (hours) after LPS challenge. Temperatures of the animals during the time course in degrees Celsius is shown for wild type mice (open squares) or ICE-deficient mice (open circles).

To examine in more detail the relationship between serum levels of IFN-γ and ICE activity in vivo, a time course after challenge of wild type and ICE-deficient mice with LPS was performed (Example 4) (FIG. 4).

FIG. 4 shows a time course increase of serum IFN-γ in wild type mice, with sustained levels of ≧17 ng/ml occurring from 9–18 hrs after LPS challenge. As predicted by the experiments discussed above, serum IFN-γ levels were significantly lower in ICE-/- mice, with a maximum of 2 ng/ml achieved over the same time period, which is approximately 15% of the level observed in wild type mice (FIG. 4).

Animals were also observed for clinical signs of sepsis and body temperature was measured at 4-hour intervals in wild type and ICE-/- mice challenged with 30 mg/kg or 100 mg/kg LPS (ICE-/- only). Results in FIG. 4 show that wild type mice experienced a significant decrease in body temperature (from 36° C. to 26° C.) within 12 hours of LPS challenge. Signs of clinical sepsis were evident and all animals expired within 24–28 hours.

In contrast, ICE-/- mice challenged with 30 mg/kg LPS experienced only a 3°–4° C. decrease in body temperature with minimal signs of distress and with no observed lethality. ICE-/- mice challenged with 100 mg/kg LPS experienced clinical symptoms, a decrease in body temperature, and mortality similar to wild type mice at the 30 mg/kg LPS dose.

The ICE Inhibitor Ac-YVAD-CHO (SEQ ID No. 1) is an Equipotent Inhibitor of IL-1β and IFN-γ Production Since the processing and secretion of biologically active IGIF is mediated by ICE, we compared the activity of a reversible ICE inhibitor (Ac-YVAD-CHO (SEQ ID NO: 1)) on IL-1β and IFN-γ production in a peripheral blood mononuclear cell (PBMC) assay (Examples 5 and 6).

Figure 5:
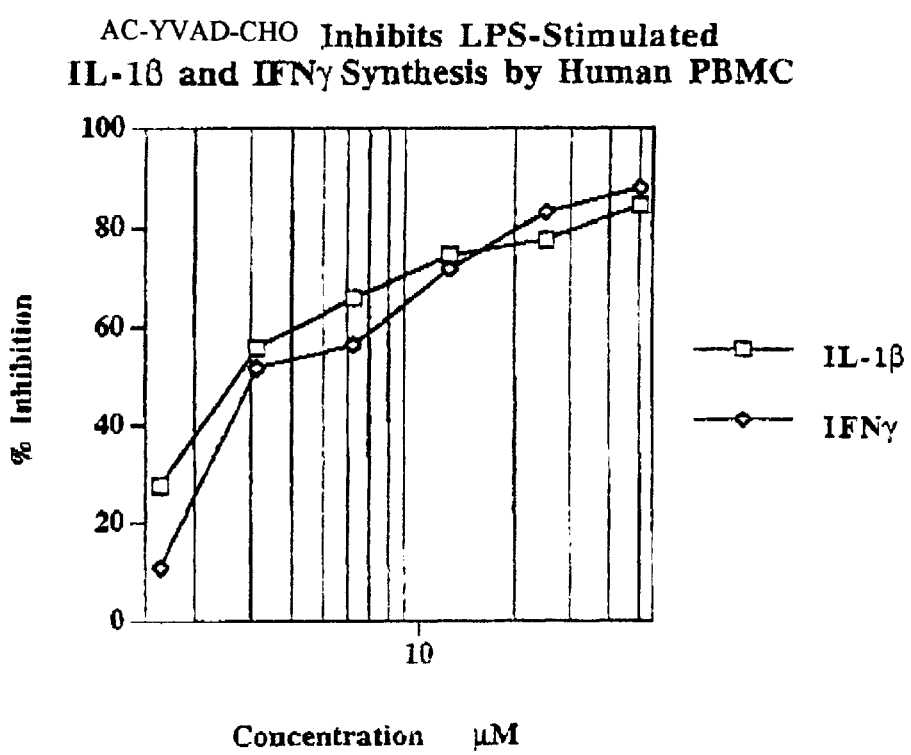
FIG. 5 The ICE inhibitor, AcYVAD-aldehyde (AcYVAD-CHO) (SEQ ID NO: 1), inhibits LPS-stimulated IL-1β and IFN-γ synthesis by human peripheral blood mononuclear cells (PBMC). Percent (%) inhibition as a function of inhibitor concentration (μM) is shown for IL-1β (open squares) and IFN-γ (open diamonds) synthesis.

Results in FIG. 5 show a similar potency for the ability of the Ac-YVAD-CHO (SEQ ID No. 1) ICE inhibitor to decrease IL-1β and IFN-γ production in human PBMCs, with an $IC_{50}$ of 2.5 μM for each. Similar results were obtained in studies with wild type mouse splenocytes.

These findings provide additional evidence that pro-IGIF is a physiological substrate for ICE and suggest that ICE inhibitors will be useful tools for controlling physiological levels of IGIF and IFN-γ.

In summary, we have found that ICE controls IGIF and IFN-γ levels in vivo and in vitro and that ICE inhibitors can decrease levels of IGIF and IFN-γ in human cells.

Compositions and Methods for Controlling IGIF and IFN-γ

The pharmaceutical compositions and methods of this invention will be useful for controlling IGIF and IFN-γ levels in vivo. The methods and compositions of this invention will thus be useful for treating or reducing the advancement, severity of effects of IGIF- and IFN-γ-mediated conditions.

Accordingly, one embodiment of this invention provides a method for decreasing IGIF production in a subject comprising the step of administering to the subject a pharmaceutical composition comprising a therapeutically effective amount of an ICE inhibitor and a pharmaceutically acceptable carrier.

Another embodiment of this invention provides a method for decreasing IFN-γ production in a subject comprising the step of administering to the subject a pharmaceutical composition comprising a therapeutically effective amount of an ICE inhibitor and a pharmaceutically acceptable carrier.

In another embodiment, the methods of this invention comprise the step of administering to a subject a pharmaceutical composition comprising an inhibitor of an ICE-related protease that is capable of cleaving pro-IGIF to active IGIF, and a pharmaceutically acceptable carrier. One such ICE-related protease is TX, as described above. This invention thus provides methods and pharmaceutical compositions for controlling IGIF and IFN-γ, levels by administering a TX inhibitor.

Other ICE-related proteases capable of processing pro-IGIF into an active IGIF form may also be found. Thus it is envisioned that inhibitors of those enzymes may be identified by those of skill in the art and will also fall within the scope of this invention.

Pharmaceutical compositions of this invention comprise an ICE inhibitor or a pharmaceutically acceptable salt thereof and a pharmaceutically acceptable carrier, adjuvant or vehicle. Such compositions may optionally comprise an additional therapeutic agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

If the pharmaceutical composition comprises only the ICE inhibitor as the active component, such methods may additionally comprise the step of administering to the subject an additional agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically acceptable carrier or adjuvant" refers to a carrier or adjuvant that may be administered to a subject, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as dα-tocopherol polyethyleneglycol 1000 succinate, or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of formulae I–V.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in *Ph. Helv.* (*Pharmacopeia Helvetica*) or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the ICE inhibitor compounds described herein are useful in a monotherapy for the prevention and treatment of IGIF or IFN-γ mediated conditions, diseases, or effects. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of an ICE inhibitor and one or more additional therapeutic or prophylactic agents, both the ICE inhibitor and the additional agent should be present at dosage levels of between about 10% to 100%, and more preferably between about 10% to 80% of the dosage normally administered in a monotherapy regimen.

When the subject is a patient, upon improvement of the patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of symptoms.

As the skilled artisan will appreciate, lower or higher doses than those recited above may be required. When the subject is a patient, specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The methods of this invention may be used for treating, or reducing the advancement, severity or effects of an IGIF- or IFN-γ-mediated inflammatory, autoimmune, infectious, proliferative, destructive bone, necrotic, and degenerative conditions, including diseases, disorders or effects, wherein the conditions are characterized by increased levels of IGIF or IFN-γ production.

Inflammatory conditions which may be treated or prevented include, but are not limited to osteoarthritis, acute pancreatitis, chronic pancreatitis, asthma, rheumatoid arthritis, inflammatory bowel disease, Crohn's disease, ulcerative collitis, cerebral ischemia, myocardial iscemia and adult respiratory distress syndrome.

Preferably, the inflammatory condition is rheumatoid arthritis, ulcerative collitis, Crohn's disease, hepatitis and adult respiratory distress syndrome.

Infectious conditions which may be treated or prevented include, but are not limited to, infectious hepatitis, sepsis, septic shock and Shigellosis.

Autoimmune conditions which may be treated or prevented include, but are not limited to, glomerulonephritis, systemic lupus erythematosus, scleroderma, chronic thyroiditis, Graves'disease, autoimmune gastritis, insulin-dependent diabetes mellitus (Type I), juvenile diabetes, autoimmune hemolytic anemia, autoimmune neutropenia, thrombocytopenia, myasthenia gravis, multiple sclerosis, psoriasis, lichenplanus, graft vs. host disease, acute dermatomyositis, eczema, primary cirrhosis, hepatitis, uveitis, Behcet's disease, acute dermatomyositis, atopic skin disease, pure red cell aplasia, aplastic anemia, amyotrophic lateral sclerosis and nephrotic syndrome.

Preferably the autoimmune condition is glomerulonephritis, insulin-dependent diabetes mellitus (Type I), juvenile diabetes, psoriasis, graft vs. host disease, including transplant rejection, and hepatitis.

Destructive bone disorders which may be treated or prevented include, but are not limited to, osteoporosis and multiple myeloma-related bone disorder.

Proliferative conditions which may be treated or prevented include, but are not limited to, acute myelogenous leukemia, chronic myelogenous leukemia, metastatic melanoma, Kaposi's sarcoma, and multiple myeloma.

The neurodegenerative conditions which may be treated or prevented by the compounds of this invention include, but are not limited to, Alzheimer's disease, Parkinson's disease and Huntington's disease.

ICE Inhibitors

ICE inhibitors which may be used according to the embodiments of this invention include those described in published PCT Application WO 95/35308, in particular, see pages 77–89, 92-93, 96-97, 102-103, 107-108, and 125–127; and co-pending U.S. applications Ser. Nos. 08/575,641, filed Dec. 20, 1995, in particular, see pages 50–53, 55–63, and 76–126; Ser. No. 08/575,648, filed Dec. 20, 1995, in particular, see pages 20–24 and 25-26; and Ser. No. 08/598, 332, filed Feb. 2, 1996, in particular, see pages 50–53, 56–63, 77–126, 166-167, 172-173 and 206.

Further examples of ICE inhibitors which may be used according to the embodiments of this invention are those found in U.S. Pat. Nos. 5,008,245; 5,411,985; 5,416,013; 5,430,128; 5,434,248; 5,462,939; 5,486,623; 5,498,616 and 5,498,695; PCT published applications WO 91/15577; WO 93/05071; WO 93/09135; WO 93/14777; WO 93/16710; WO 94/03480; WO 95/05192; WO 95/26958; WO 95/29672; WO 95/33751 and WO 96/03982; Foreign patent documents EP 519,748; EP 528,487; EP 529,713; EP 533, 226; EP 547,699; EP 618,223; EP 623,592; EP 623,606; EP 628,550; EP 644,197; EP 644,198; AU 64514/94; DE 195 34 164; and GB 2,292,149; and other documents, such as M. Ator, "Peptide and Non-peptide Inhibitors of Interleukin-1β Converting Enzyme", *Cambridae Healthtech Institute (Inflammatory Cytokine Antaaonists Targets, Strategies, and Indication)*, (1994), see pyridazines, pages 2–4; peptides, pages 5–13; M. Ator and R. Dolle, "Interleukin-1β Converting Enzyme: Biology and the Chemistry of Inhibitors", *Curr. Pharm. Design*, I, pp. 191–210 (1995); K. Chapman, "Synthesis of a Potent, Reversible Inhibitor of Interleukin-1β Converting Enzyme", *Bioorg. Med. Chem. Lett.*, 2, pp. 613–618 (1992); R. Dolle et al., "Aspartyl α-((1-Phenyl-3-(trifluoromethyl)-pyrazol-5-yl)oxy)methyl Ketones as Interleukin-1β Converting Enzyme Inhibitors. Significance of the $P_1$ and $P_3$ Amido Nitrogers for Enzyme-Peptide Inhibitor Binding", *J. Med. Chem.*, 37, pp. 3863–3865 (1994), see page 364; R. Dolle et al., "Aspartyl α-((Diphenylphosphinyl)oxy)methyl Ketones as Novel Inhibitors of Interleukin-1β Converting Enzyme. Utility of the Diphenylphosphinic Acid Leaving Group for the Inhibition of Cysteine Proteases", *J. Med. Chem.*, 38, pp. 220–222 (1995), see page 221; R. Dolle et al., "$P_1$ Aspartate-Based Peptide α-((2,6-Dichlorobenzoyl)oxy)methyl Ketones as Potent Time-Dependent Inhibitors of Interleukin-1β-Converting Enzyme", *J. Med. Chem.*, 37, pp. 563–564 (1994), see page 563; R. Dolle et al., "First Examples of Peptidomimetic Inhibitors of Interleukin-1β Converting Enzyme", *J. Med. Chem.*, 39, pp. 2438–2440 (1996); P. Elford et al., "Reduction of Inflammation and Pyrexia in the Rate by Oral Administration of SDZ 224-015, an Inhibitor of the Interleukin-1β Converting Enzyme", *Brit. J. Pharm.*, 115, pp. 601–606 (1995); I. Fauszt et al., "Inhibition of Interleukin-1β Converting Enzyme by Peptide Derivatives", *Proc. of the 13th Am. Peptide Symp.*, June 20–25, 1993, Hodges, R. S. and Smith, J. A., Eds., *Peptides*, pp. 589–591 (1994); T. Graybill et al., "Preparation and evaluation of peptidic aspartyl hemiacetals as reversible inhibitors of interleukin-1β converting enzyme (ICE)", *Int. J. Peptide Protein Res.*, 44, pp. 173–182 (1994); T. Graybill et al., "Synthesis and Evaluation of Diacylhydrazines as Inhibitors of the Interleukin-1β Converting Enzyme (ICE)", *Bioorg. Med. Chem, Lett.*, 5, pp. 1197–1202 (1995); B. Miller et al., "Inhibition of Mature IL-1β Production in Murine Macrophages and a Murine Model of Inflammation by WIN 67694, an Inhibitor of IL-1β Converting Enzyme", *J. Immunol.*, 154, pp. 1331–1338 (1995), see page 1332; A. Mjalli et al., "Phenylalkyl Ketones as Potent Reversible Inhibitors of Interleukin-1β Converting Enzyme", *Bioorg, Med. Chem. Lett.*, 3, pp. 2689–2692 (1993); A. Mjalli et al., "Synthesis of a Peptidyl 2,2-Difluoro-4-Phenylbutyl Ketone and its Evaluation as an Inhibitor of Interleukin-1β Converting Enzyme", *Bioorg. Med. Chem. Lett.*, 3, pp. 2693–2698 (1993); A. Mjalli et al., "Activated Ketones as Potent Reversible Inhibitors of Interleukin-1β Converting Enzyme", *Bioorg Med. Chem. Lett.*, 4, pp. 1965–1968 (1994), see page 1967; M. Mullican et al., "The Synthesis and Evaluation of Peptidyl Aspartyl Aldehydes as Inhibitors of ICE", *Bioorg. Med. Chem. Lett.*, 4, pp. 2359–2364 (1994), see page 2362; C. Ray et al., "Viral Inhibition of Inflammation: Cowpox Virus Encodes an Inhibitor of the Interleukin-1β Converting Enzyme", *Cell*, 69, pp. 597–604 (1992); R. Robinson and K. Donahue, "Synthesis of a Peptidyl Difluoro Ketone Bearing the Aspartic Acid Side Chain: An Inhibitor of Interleukin-1β Converting Enzyme", J. Org. Chem., 57, pp. 7309–7314 (1992), see page 7309; M. Salvatore et al., "L-741,494, A Fungal Metabolite that is an Inhibitor of Interleulin-1β Converting Enzyme", J. Nat. Prods., 57, pp. 755–760 (1994); S. Schmidt et al., "Synthesis and Evaluation of aspartyl α-Chloro-, α-Aryloxy-, and α-Arylacyloxymethyl Ketones as Inhibitors of Interleukin-1β Converting Enzyme", Am. Chem. Soc. (208th Natl. Mtg.), MEDI 4, Aug. 21–25 (1994); N. Thornberry et al., "Inactivation of Interleukin-1β Converting Enzyme by Peptide (Acyloxy)methyl Ketones", Biochemistry, 33, pp. 3934–3940 (1994), see pages 3937–3938; E. Tsukuda et al., "EI-1507 and -2, Novel Interleukin-1β Converting Enzyme Inhibitors Produced by Streptomyces sp. E-1507", J. Antibiotics, 49, pp. 333–339 (1996).

All of the cited documents are incorporated by reference herein. The ICE inhibitors cited in these documents may be used alone or in combination, in one or more embodiments of this invention.

Selected examples of such ICE inhibitors include but are not limited to the following compounds: A1, A4, A5, A6, A7, A8, A9, A1, A11, A12, A13, A14, A15, A16, A17, A18, A19, A20, A22, A23, A24, A25, A27, A28, 213e, 214c, 214e, 214e, 217c, 217d, 217e, 220b, 223b, 223e, 226e, 227e, 246, 257, 265, 280, 281, 282, 283, 284, 285, 286, 287, 302, 304a, 308a, 308b, 404, 405, 406, 407, 408, 409, 410, 411, 412, 413, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 481s, 482, 482s, 483, 484, 485, 486, 487, 488, 489, 490, 491, 493, 494, 495, 496, 497, 498, 499, 605a, 605b, 605c, 605d, 605e, 605f, 605g, 605h, 605i, 605j, 605m, 605n, 605o, 605p, 605q, 605s, 605t, 605v, 609a, 609b, 619, 620, 621, 622, 623, 624, 625, 626, 627, 628, 629, 630, 631, 632, 633, 634, 635, 813e, 814c, 817c, 817d, 817e, 820b, 823b, 823e, 826e, 827e, 880, 881, 882, 883, 884, 885, 886, 887, 902, 904a, 907a, 907b, 1004, 1005, 1006, 1007, 1008, 1009, 1010, 1011, 1012, 1013, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 11060, 1061, 1062, 1063, 1064, 1065, 1066, 1067, 1068, 1069, 1070, 1071, 1073, 1074, 1075, 1076, 1077, 1078, 1079, 1080, 1081, 1081s, 1082, 1082s, 1083, 1084, 1085, 1086, 1087, 1088, 1089, 1090, 1091, 1093, 1094, 1095, 1096, 1097, 1098, 1099, 2001, 2002, 2100a, 2100b, 2100c, 2100d, 2100e and 2201.

At this point in time, a more preferred pharmaceutical composition comprises compound 412.

Figure 6:
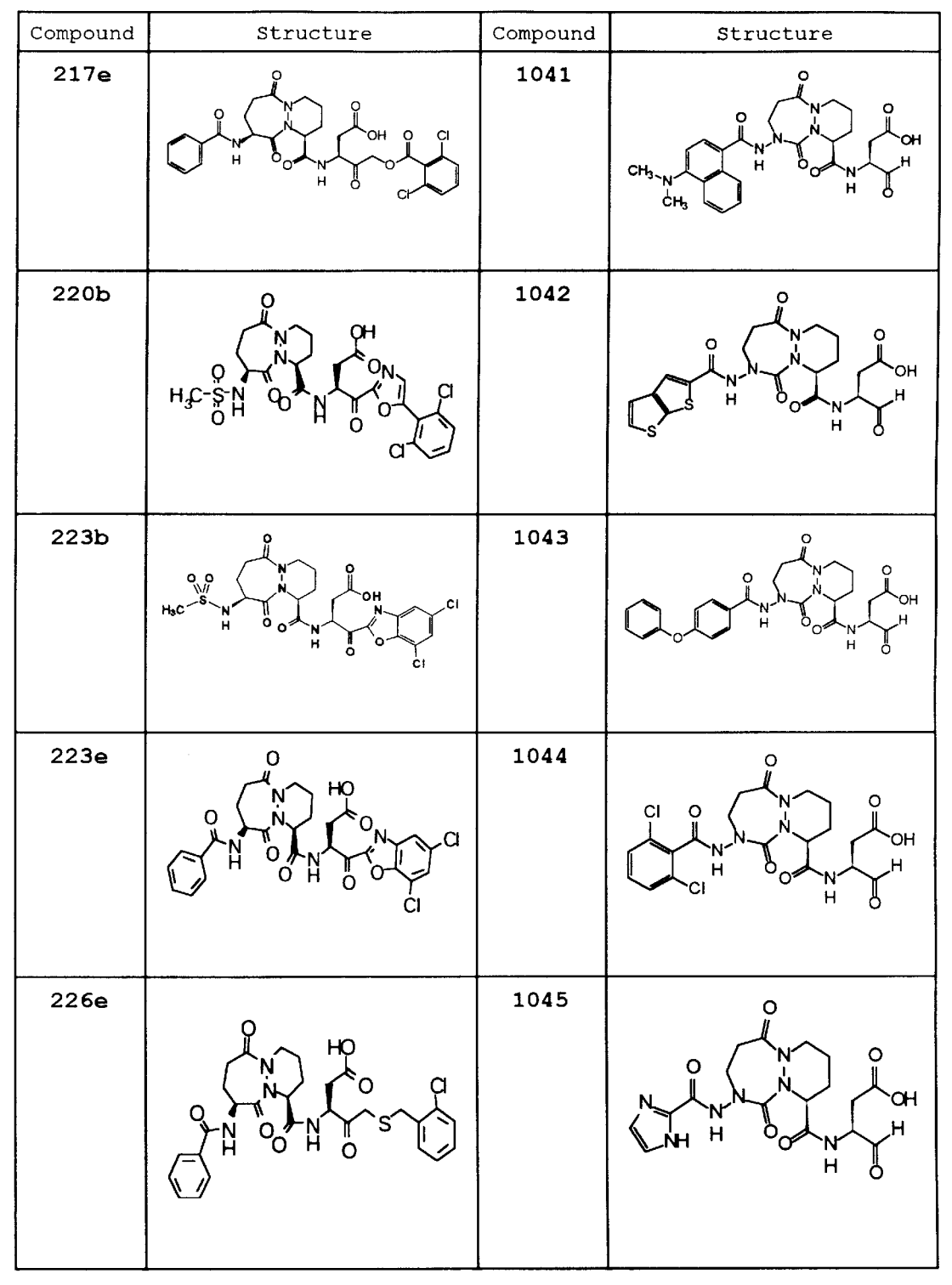
Figure 6:
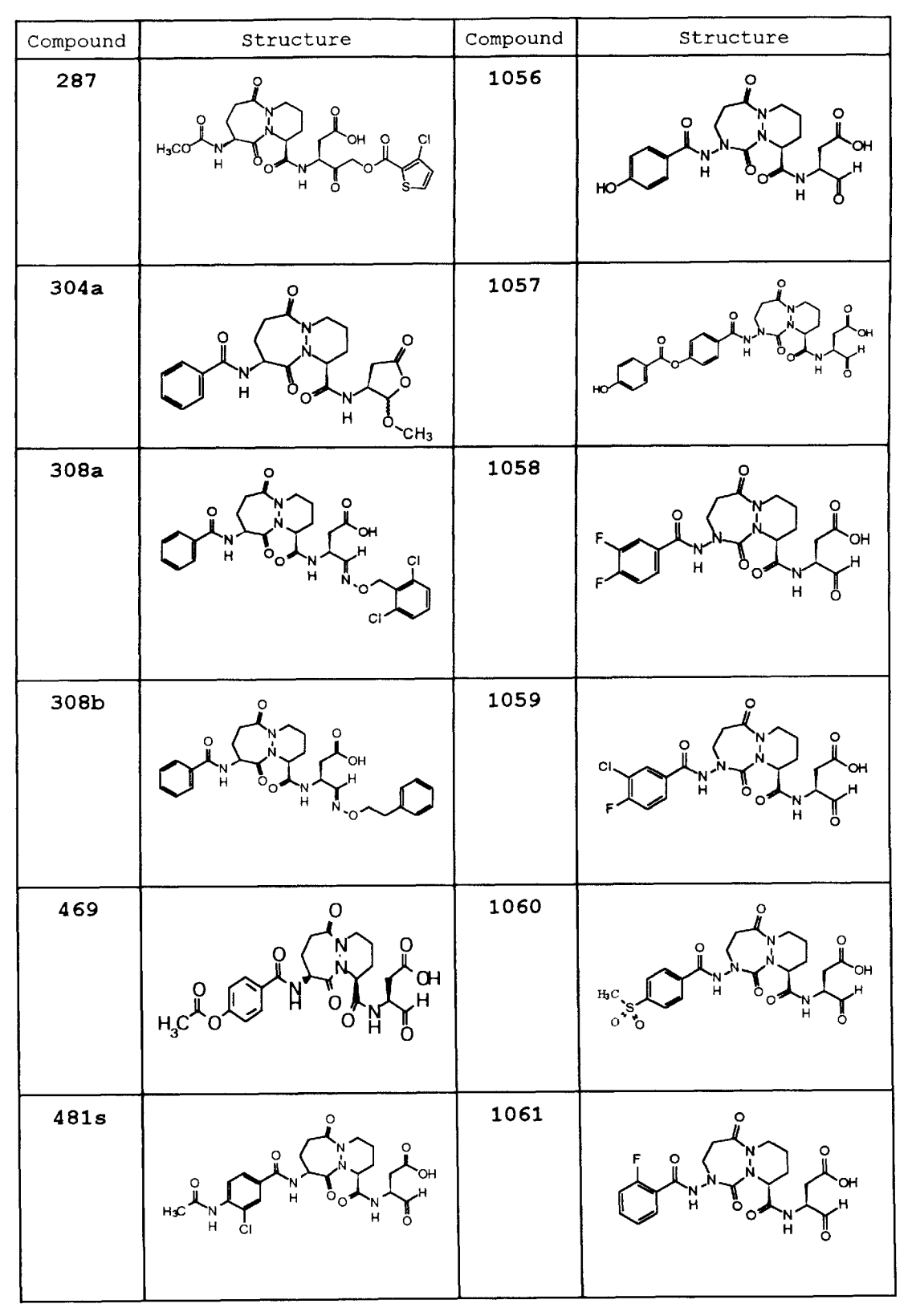
Figure 6:
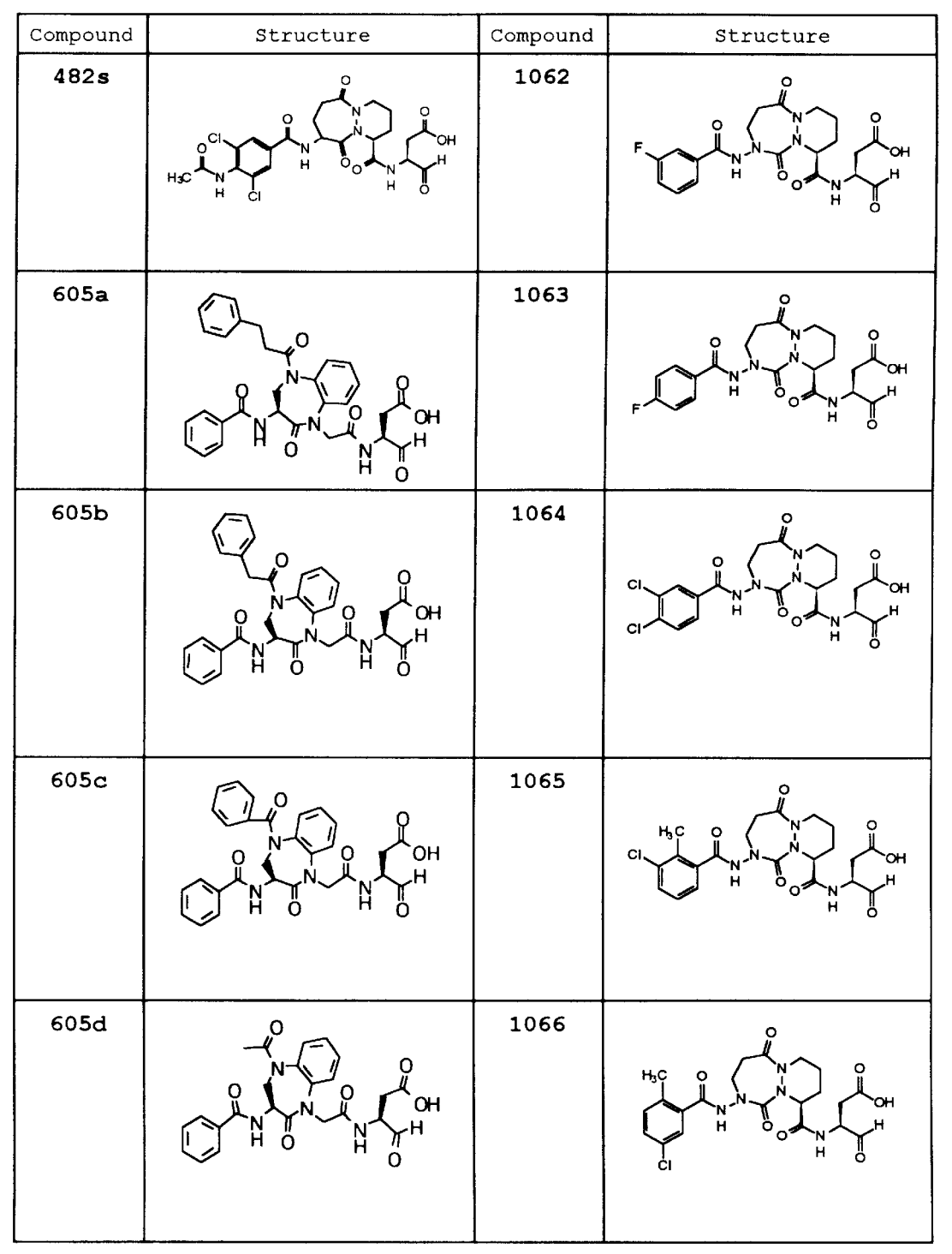
Figure 6:
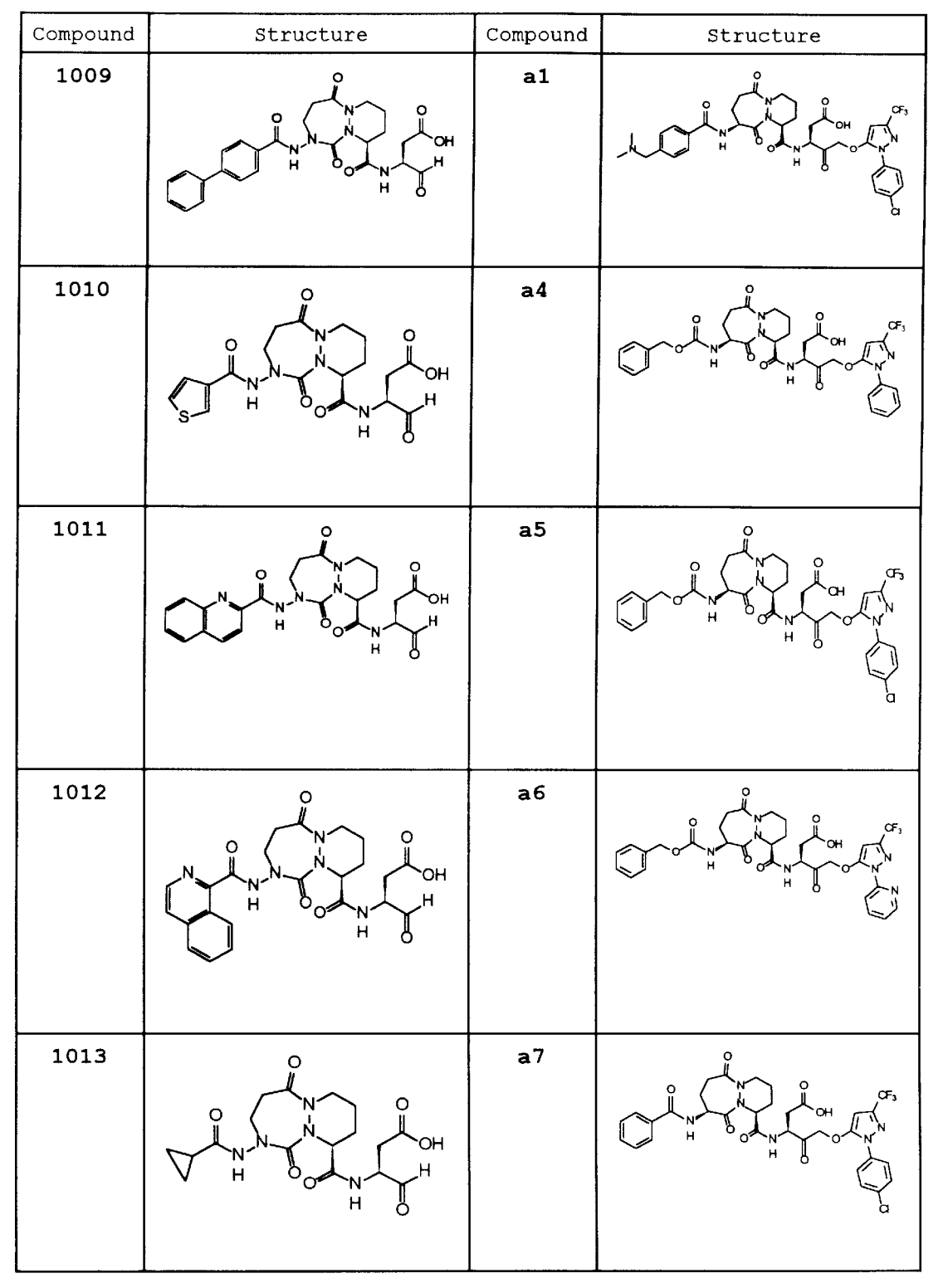
Figure 6:
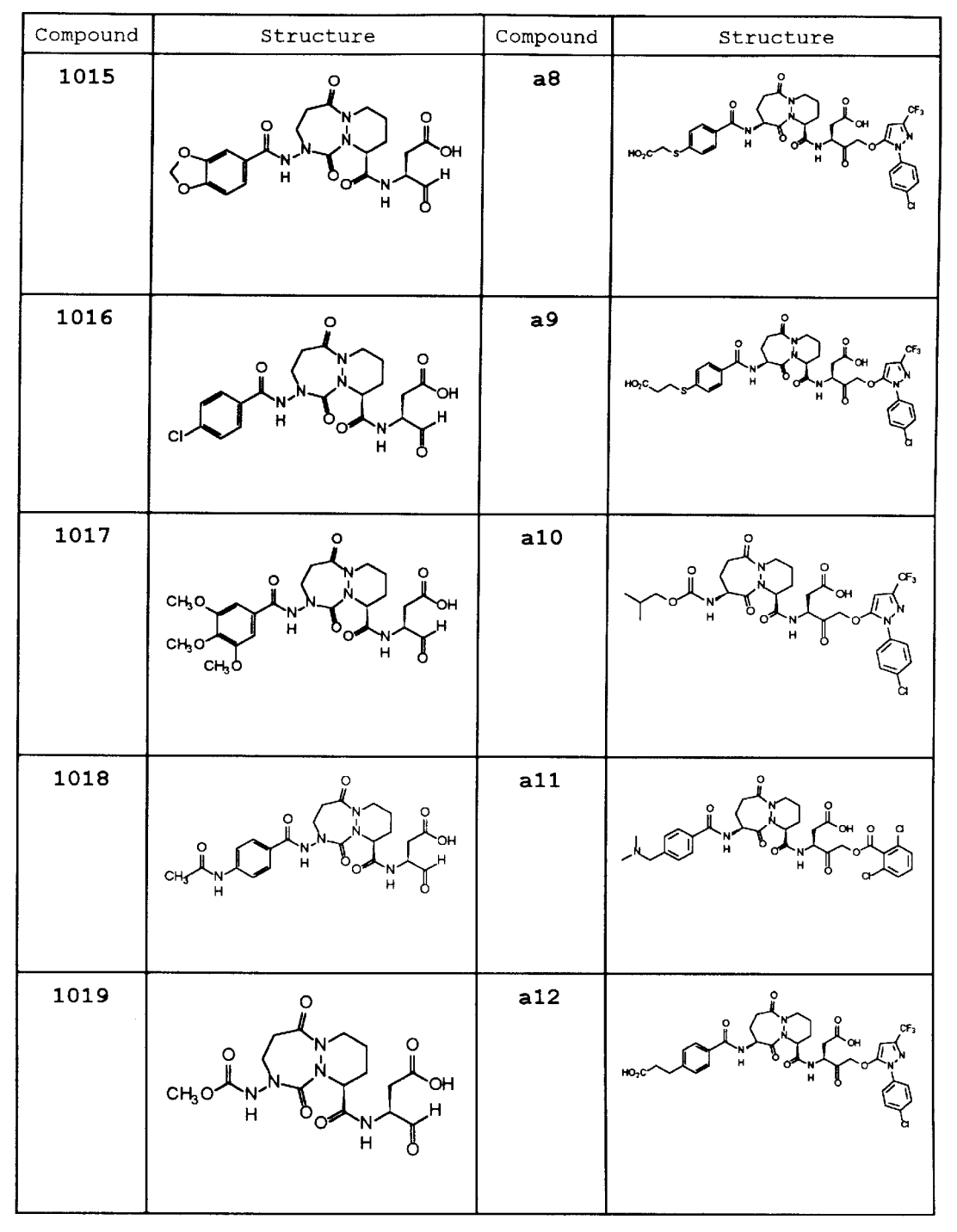
Figure 6:
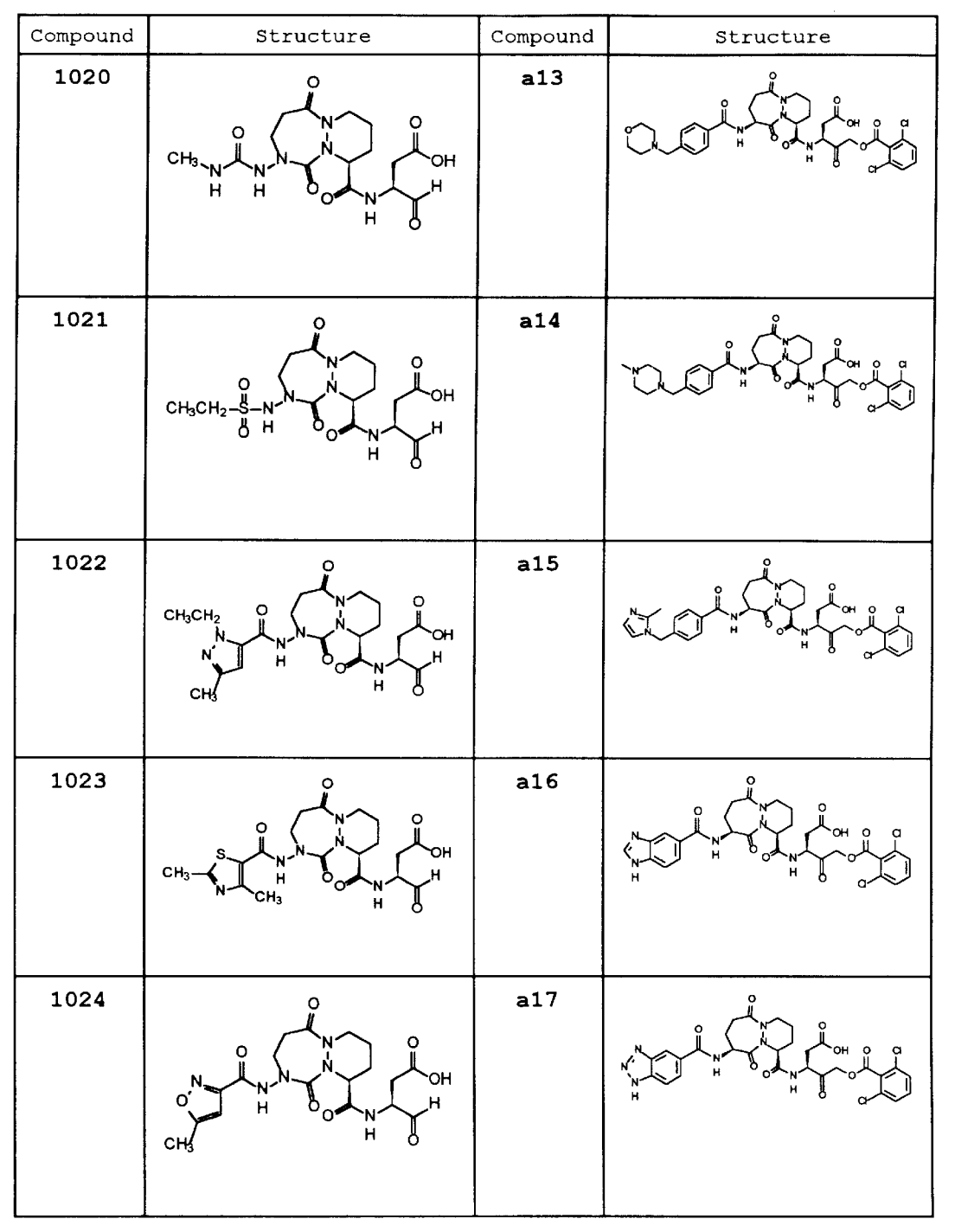
Figure 6:
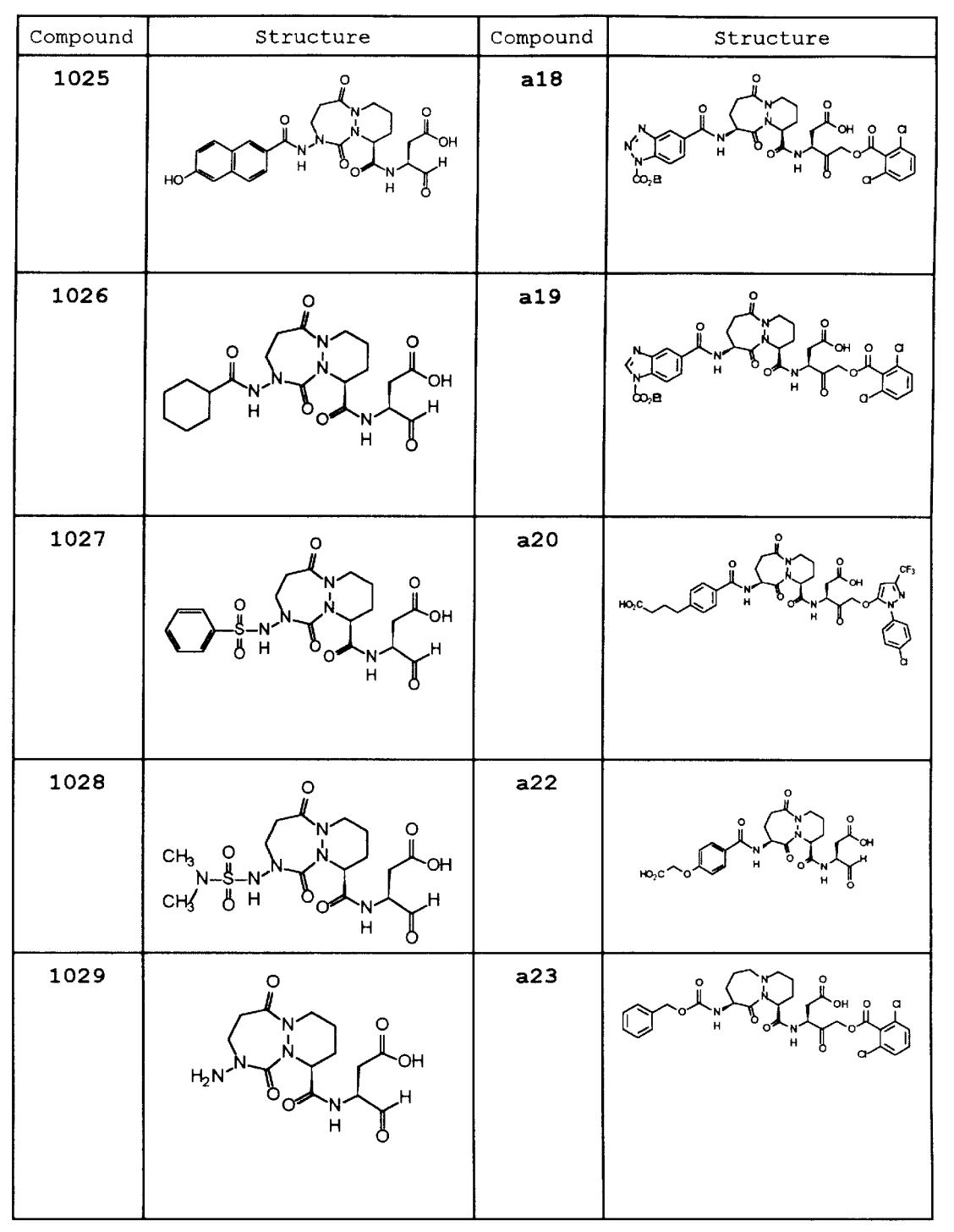
Figure 6:
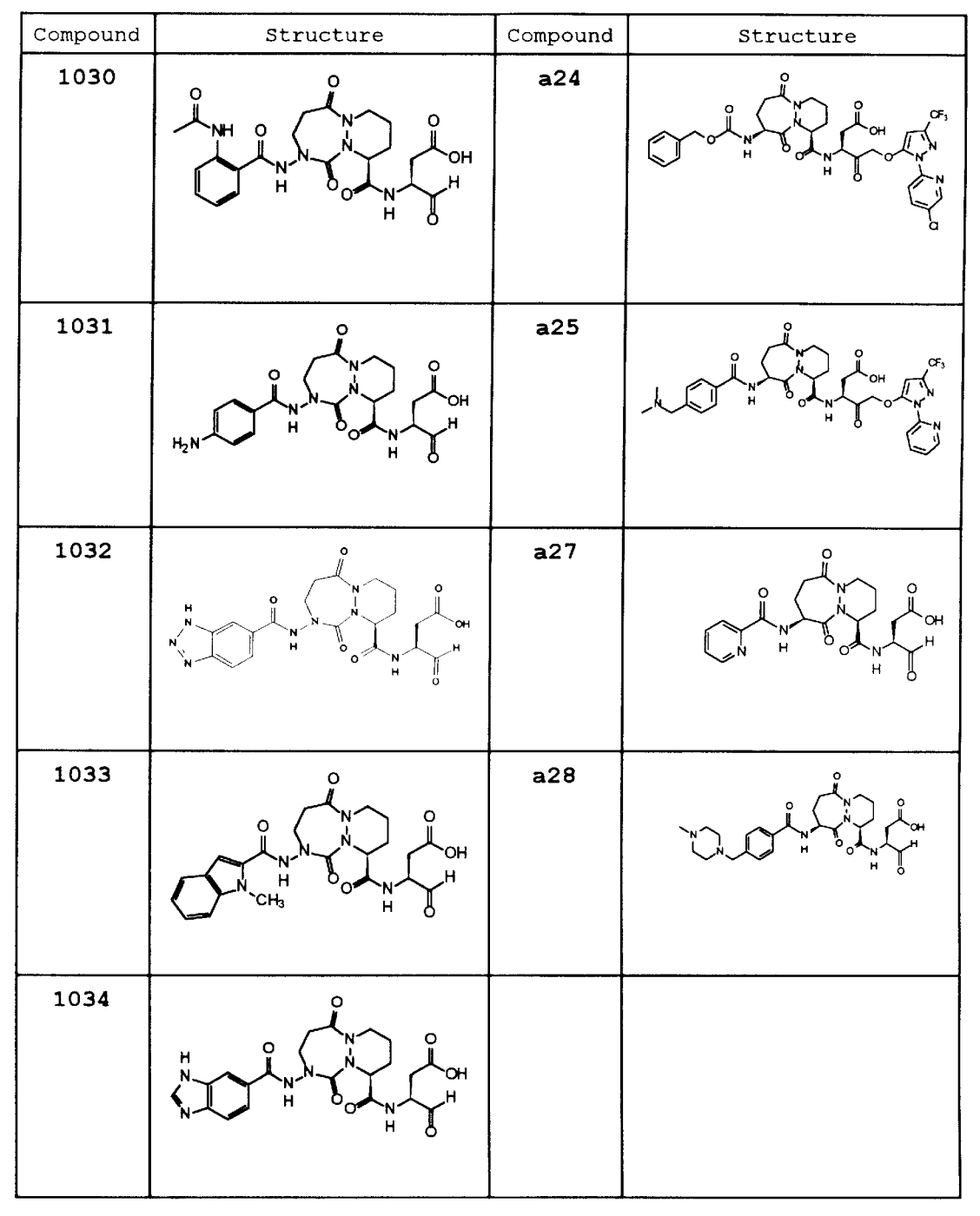
Figure 6:
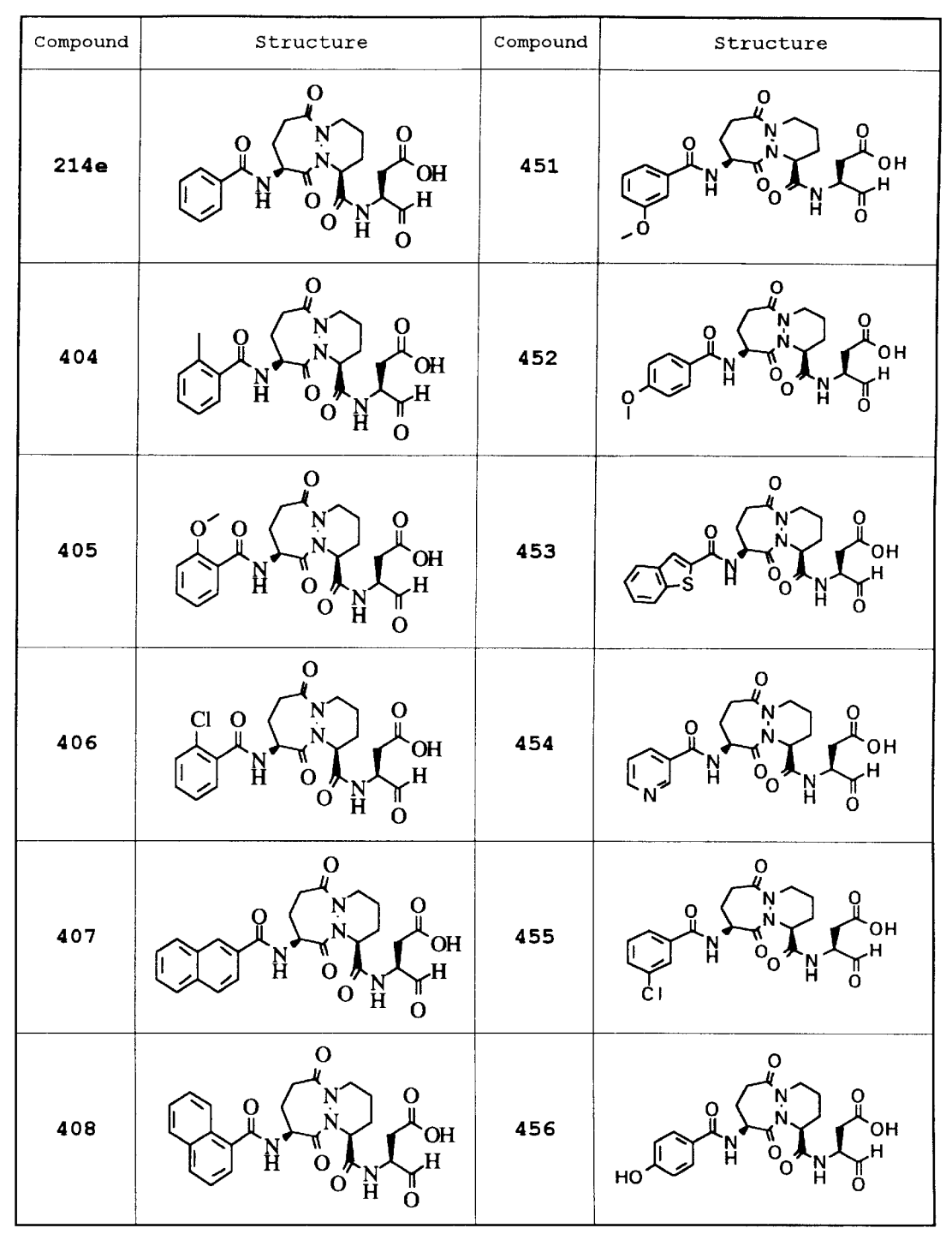
Figure 6:
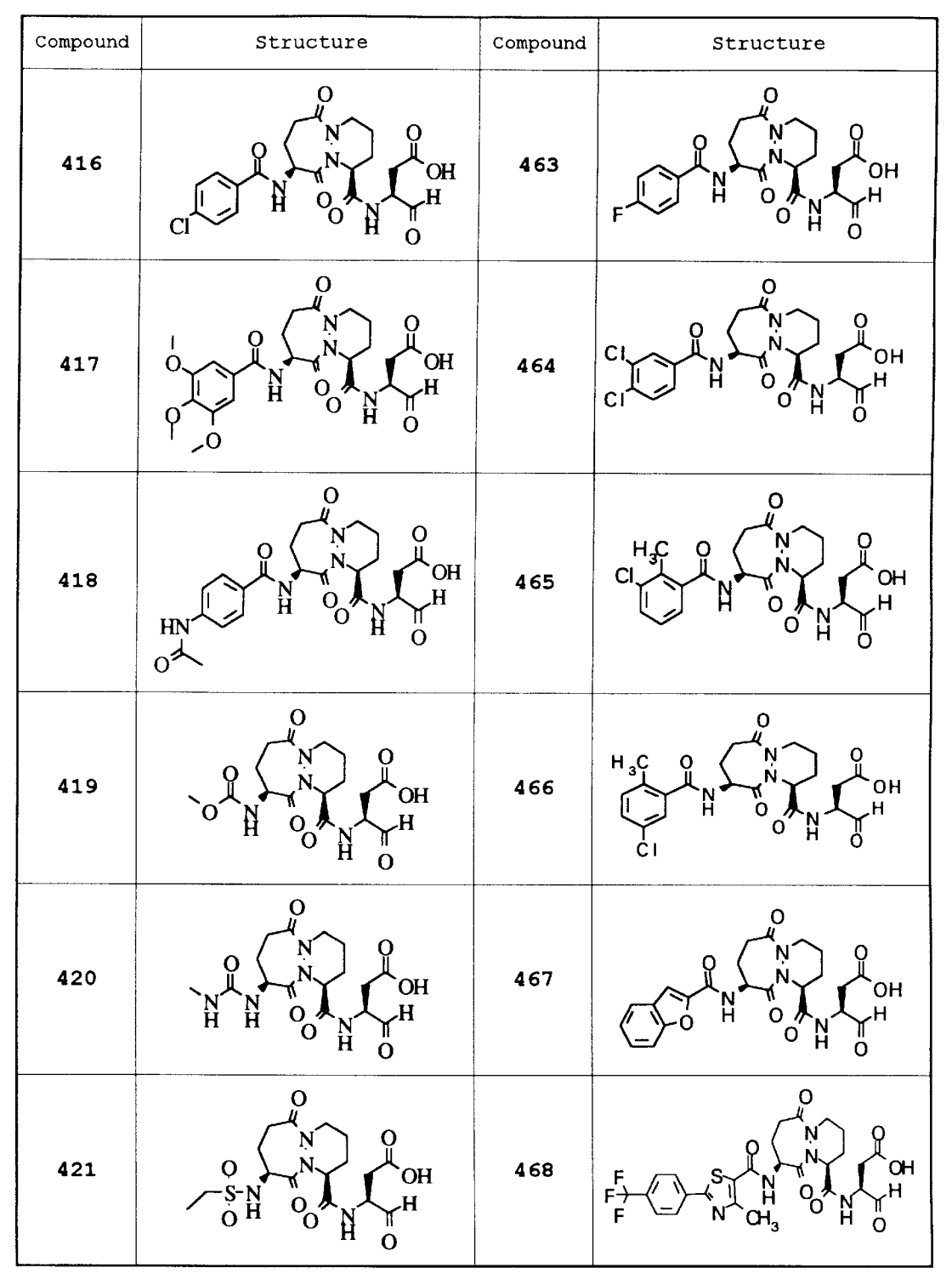
Figure 6:
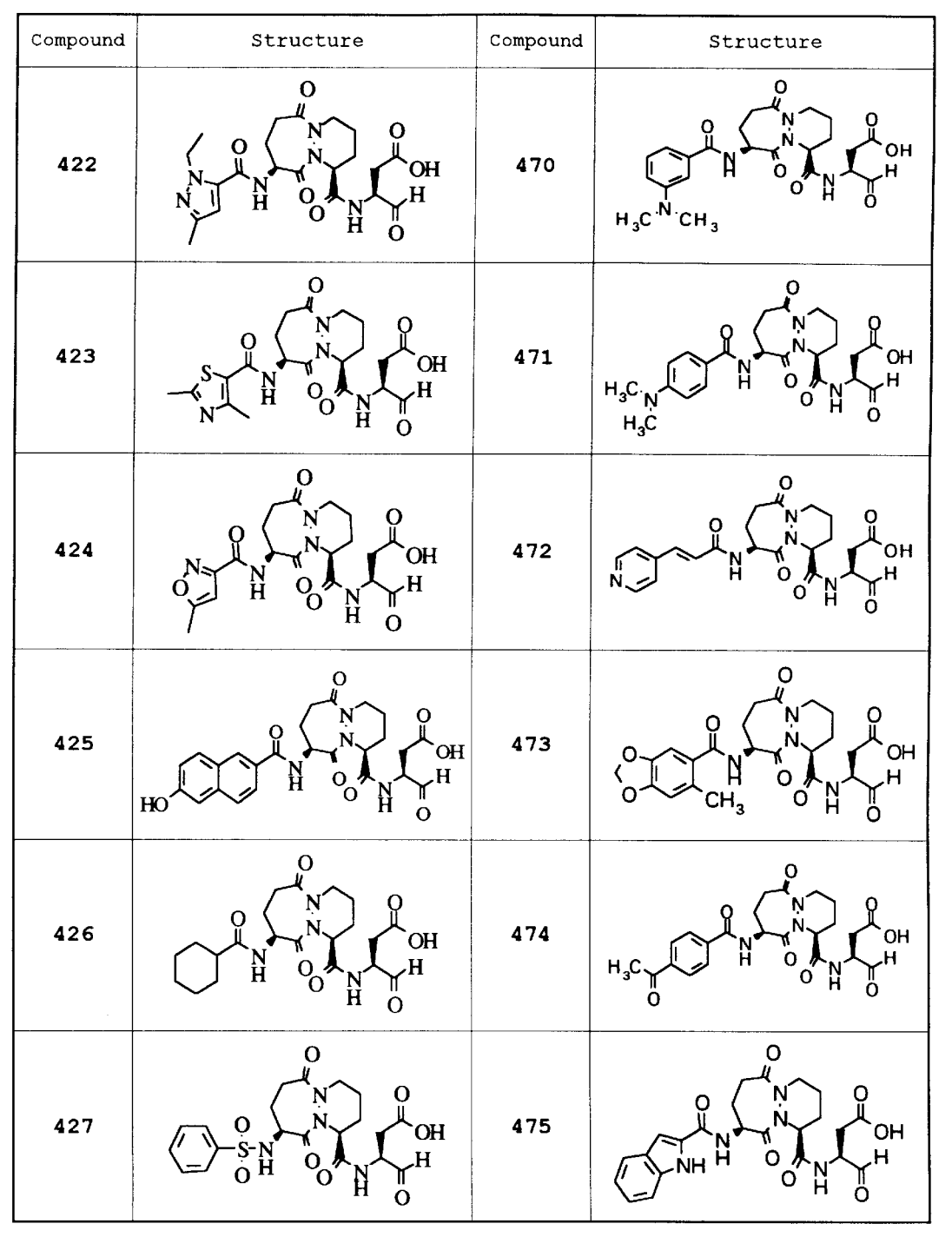
Figure 6:
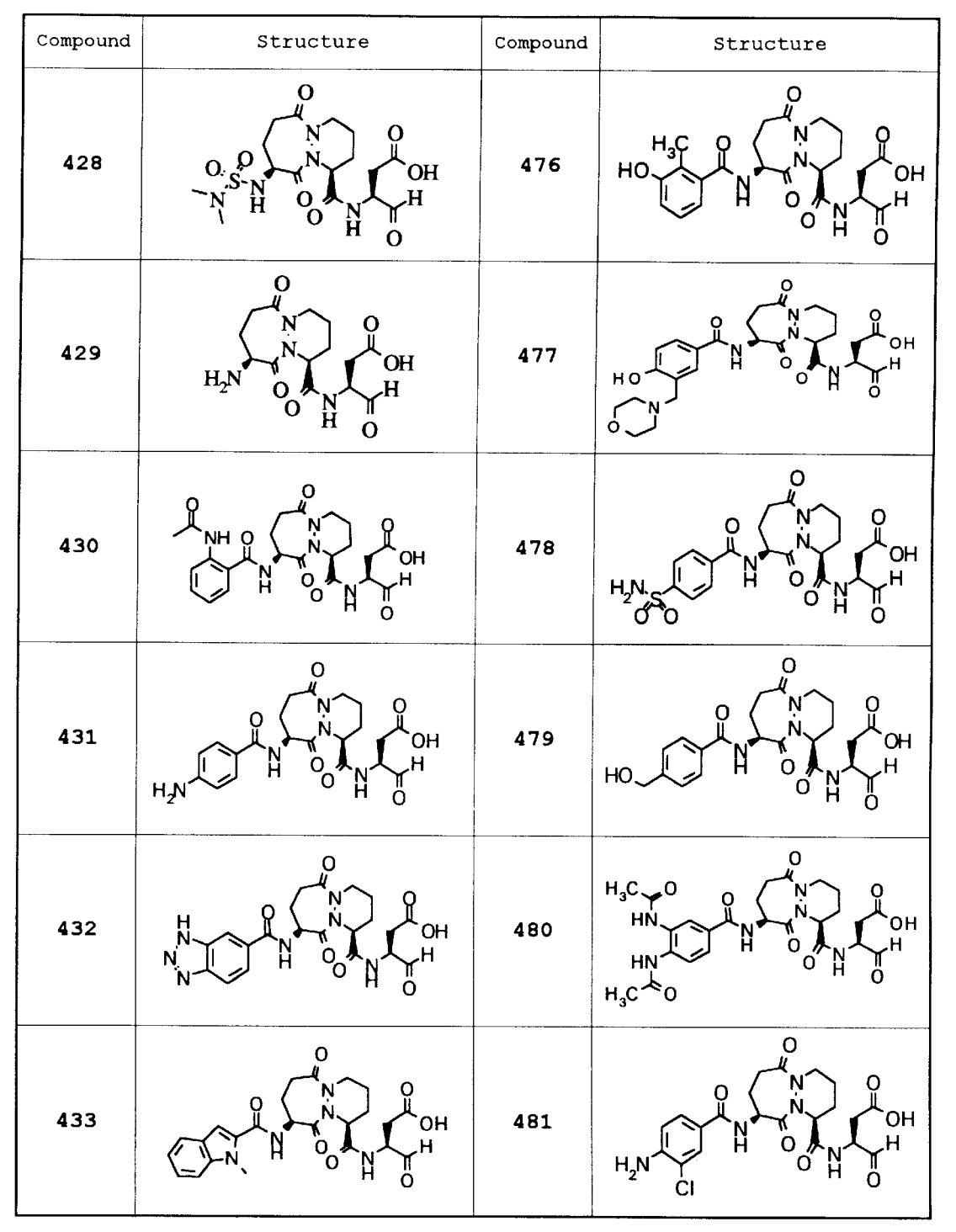
Figure 6:
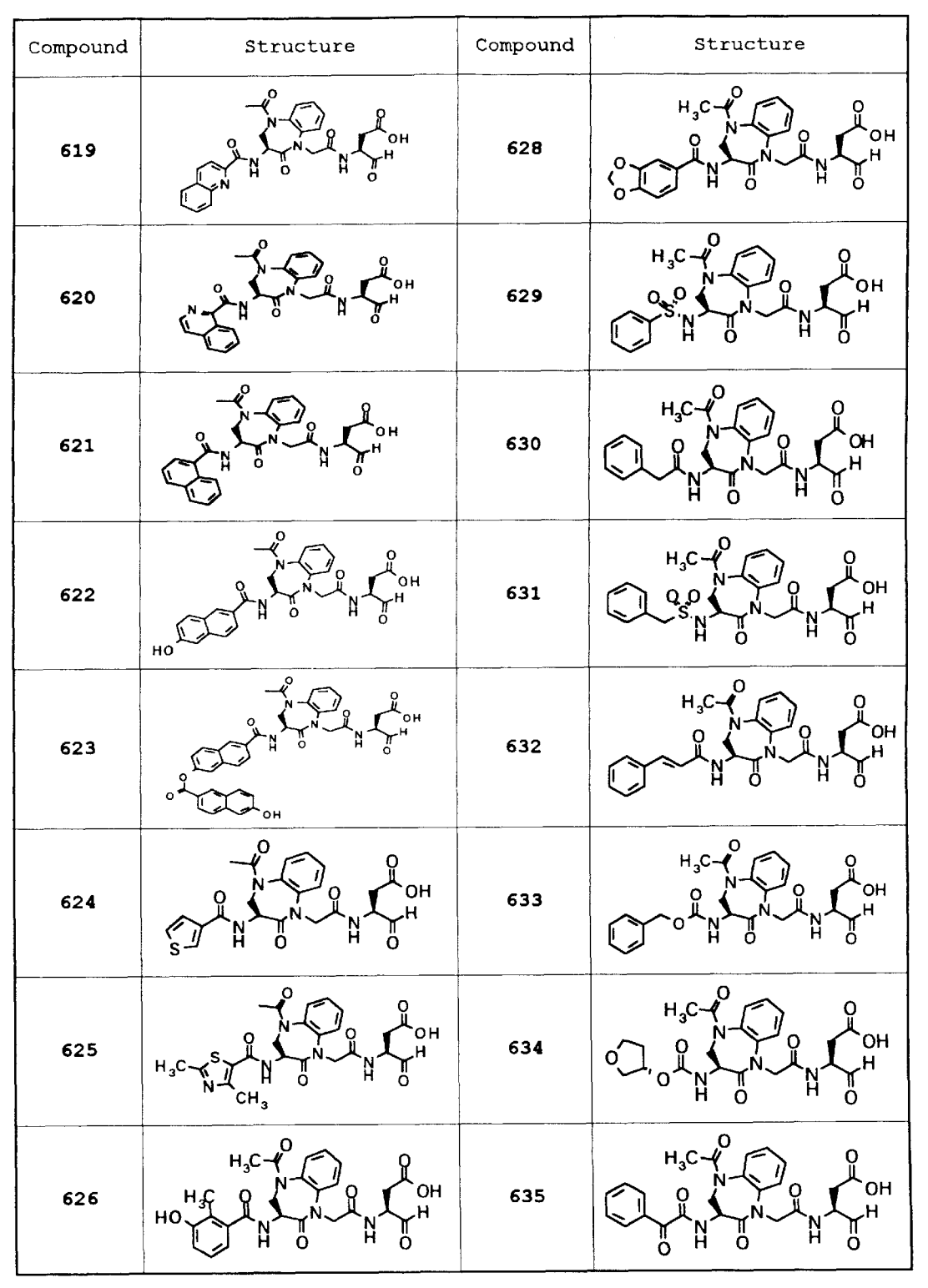

The structures of the above selected compounds may be found in FIG. 6. These compounds may be prepared by standard methodologies. Further details about the preparation of such compounds may be found in the documents incorporated herein (in particular, see the Examples in published PCT Applications WO 95/35308 and WO 95/33751 and copending U.S. applications Ser. Nos. 08/575,641, filed Dec. 20, 1995, Ser. No. 08/575,648, filed Dec. 20, 1995 and Ser. No. 08/598,332, filed Feb. 2, 1996.

Preferred ICE inhibitors which may be used according to the embodiments of this invention are those of formula (I):

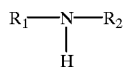

wherein:

$R_1$ is selected from the group consisting of the following formulae:

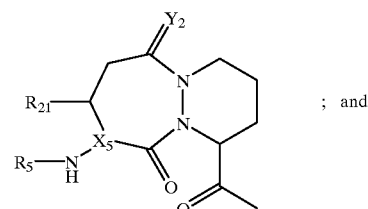

(e10)

; and

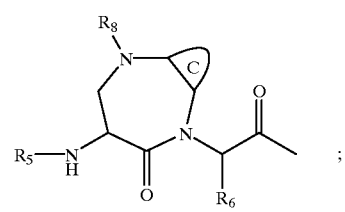

(w2)

ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_2$ is:

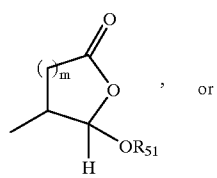

(a)

, or

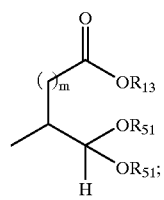

(b)

m is 1 or 2;
each $R_5$ is independently selected from the group consisting of:
—C(O)—$R_{10}$,
—C(O)O—$R_9$,
—C(O)—N($R_{10}$)($R_{10}$)
—S(O)$_2$—$R_9$,
—S(O)$_2$—NH—$R_{10}$,
—C(O)—CH$_2$—O—$R_9$,
—C(O)C(O)—$R_{10}$,
—$R_9$,
—H,
—C(O)C(O)—O$R_{10}$, and
—C(O)C(O)—N($R_9$)($R_{10}$);

$X_5$ is

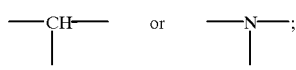

$Y_2$ is $H_2$ or O;

$R_6$ is selected from the group consisting of —H and —$CH_3$;

$R_8$ is selected from the group consisting of:
—C(O)—$R_{10}$,
—C(O)O—$R_9$,
—C(O)—N(H)—$R_{10}$,
—S(O)$_2$—$R_9$,
—S(O)$_2$—NH—$R_{10}$,
—C(O)—$CH_2$—O$R_{10}$,
—C(O)C(O)—$R_{10}$;
—C(O)—$CH_2$N($R_{10}$)($R_{10}$),
—C(O)—$CH_2$C(O)—O—$R_9$,
—C(O)—$CH_2$C(O)—$R_9$,
—H, and
—C(O)—C(O)—O$R_{10}$;

each $R_9$ is independently selected from the group consisting of —Ar$_3$ and a —$C_{1-6}$ straight or branched alkyl group that is optionally substituted with Ar$_3$, wherein the —$C_{1-6}$ alkyl group is optionally unsaturated;

each $R_{10}$ is independently selected from the group consisting of —H, —Ar$_3$, a —$C_{3-6}$ cycloalkyl groap, and a —$C_{1-6}$ straight or branched alkyl group optionally substituted with Ar$_3$, wherein the —$C_{1-6}$ alkyl group is optionally unsaturated;

$R_{13}$ is selected from the group consisting of H, Ar$_3$, and a $C_{1-6}$ straight or branched alkyl group optionally substituted with Ar$_3$, —CONH$_2$, —OR$_5$, —OH, —OR$_9$, or —CO$_2$H;

each $R_{51}$ is independently selected from the group consisting of $R_9$, —C(O)—$R_9$, —C(O)—N(H)—$R_9$, or each $R_{51}$ taken together forms a saturated 4–8 member carbocyclic ring or heterocyclic ring containing —O—, —S—, or —NH—;

each $R_{21}$ is independently selected from the group consisting of —H or a —$C_{1-6}$ straight or branched alkyl group;

each Ar$_3$ is a cyclic group independently selected from the set consisting of an aryl group which contains 6, 10, 12, or 14 carbon atoms and between 1 and 3 rings; and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, said heterocycle group optionally containing one or more double bonds, said heterocycle cgroup optionally comprising one or more aromatic rings, and said cyclic group optionally being singly or multiply substituted by —Q$_1$;

each $Q_1$ is independently selected from the group consisting of —NH$_2$, —CO$_2$H, —Cl, —F, —Br, —I, —NO$_2$, —CN, =O, —OH, —perfluoro $C_{1-3}$ alkyl, R$_5$, —OR$_5$, —NHR$_5$, OR$_9$, —N(Rg)(R$_{10}$), R$_9$, —C(O)—$R_{10}$, and

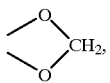

provided that when —Ar$_3$ is substituted with a —Q$_1$ group which comprises one or more additiona —Ar$_3$ groups, said additional —Ar$_3$ groups are not substituted with another —Ar$_3$.

More preferably:

m is 1;

$R_{13}$ is H or a —$C_{1-4}$ straight or branched alkyl group optionally substituted with —Ar$_3$, —OH, —OR$_9$, or —CO$_2$H, wherein the $R_9$ is a —$C_{1-4}$ branched or straight alkyl group, wherein Ar$_3$ is morpholinyl or phenyl, wherein the phenyl is optionally substituted with $Q_1$;

$R_{21}$ is —H or —$CH_3$;

$R_{51}$ is a $C_{1-6}$ straight or branched alkyl group optionally substituted with Ar$_3$, wherein Ar$_3$ is phenyl, optionally substituted by —$Q_1$;

each Ar$_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by —$Q_1$;

each $Q_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —N(R$_9$)(R$_{10}$), and

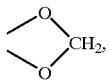

wherein each $R_9$ and $R_{10}$ are independently a —$C_{1-6}$ straight or branched alkyl group optionally substituted with Ar$_3$ wherein Ar$_3$ is phenyl;

provided that when —Ar$_3$ is substituted with a —Q$_1$ group which comprises one or more additional —Ar$_3$ groups, said additional —Ar$_3$ groups are not substituted with another —Ar$_3$.

Most preferably the ICE inhibitors of formula (I) are those wherein $R_1$ is (w2) and the other substituents are as described above.

Other most preferred ICE inhibitors of formula (I) are those wherein $R_1$ is (e10) and $X_5$ is CH.

Alternatively, in these most preferred ICE inhibitors, $R_1$ is (e10) and $X_5$ is N.

Other preferred ICE inhibitors that may be used according to the embodiments of this invention are those of formula (II):

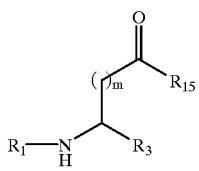

(II)

wherein:
m is 1 or 2;
$R_1$ is selected from the group consisting of the following formulae:

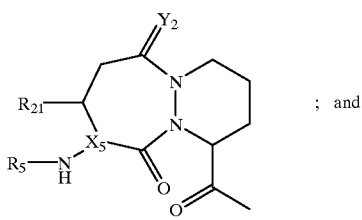

(e10); and

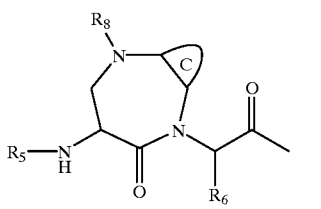

(w2);

ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_3$ is selected from the group consisting of:
—CN,
—C(O)—H,
—C(O)—CH$_2$—T$_1$—R$_{11}$,
—C(O)—CH$_2$—F,
—C=N—O—R$_9$, and
—CO—Ar$_2$;

each $R_5$ is independently selected from the group consisting of:
—C(O)—R$_{10}$,
—C(O)O—R$_9$,
—C(O)—N(R$_{10}$)(R$_{10}$)
—S(O)$_2$—R$_9$,
—S(O)$_2$—NH—R$_{10}$,
—C(O)—CH$_2$—O—R$_9$,
—C(O)C(O)—R$_{10}$,
—R$_9$,
—H,
—C(O)C(O)—OR$_{10}$, and
—C(O)C(O)—N(R$_9$)(R$_{10}$);

$X_5$ is

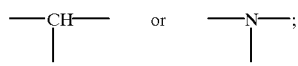

$Y_2$ is H$_2$ or O;
each $T_1$ is independently selected from the group consisting of —O—, —S—, —S(O)—, and —S(O)$_2$—;

$R_6$ is selected from the group consisting of —H and —CH$_3$;
$R_8$ is selected from the group consisting of:
—C(O)—R$_{10}$,
—C(O)O—R$_9$,
—C(O)—NH—R$_{10}$,
—S(O)$_2$—R$_9$,
—S(O)$_2$—NH—R$_{10}$,
—C(O)—CH$_2$—OR$_{10}$,
—C(O)C(O)—R$_{10}$,
—C(O)—CH$_2$—N(R$_{10}$)(R$_{10}$)
—C(O)—CH$_2$C(O)—O—R$_9$,
—C(O)—CH$_2$C(O)—R$_9$,
—H, and
—C(O)—C(O)—OR$_{10}$;

each $R_9$ is independently selected from the group consisting of —Ar$_3$ and a —C$_{1-6}$ straight or branched alkyl group that is optionally substituted with Ar$_3$, wherein the —C$_{1-6}$ alkyl group is optionally unsaturated;

each $R_{10}$ is independently selected from the group consisting of —H, —Ar$_3$, a C$_{3-6}$ cycloalkyl group, and a —C$_{1-6}$ straight or branched alkyl group optionally substituted with Ar$_3$, wherein the —C$_{1-6}$ alkyl group is optionally unsaturated;

each $R_{11}$ is independently selected from the group consisting of:
—Ar$_4$,
—(CH$_2$)$_{1-3}$—Ar$_4$,
—H, and
—C(O)—Ar$_4$;

$R_{15}$ is selected from the group consisting of —OH, —OAr$_3$, —N(H)—OH, and a —OC$_{1-6}$ straight or branched alkyl group optionally substituted with —Ar$_3$, —CONH$_2$, —OR$_5$, —OH, —OR$_9$, or —CO$_2$H;

each $R_{21}$ is independently selected from the group consisting of —H or a —C$_{1-6}$ straight or branched alkyl group;

Ar$_2$ is independently selected from the following group, in which any ring may optionally be singly or multiply substituted by —Q$_1$:

(hh)

and (ii)

wherein each Y is independently selected from the group consisting of O and S;

each Ar$_3$ is a cyclic group independently selected from the set consisting of an aryl group which contains 6, 10, 12, or 14 carbon atoms and between 1 and 3 rings; and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by —Q$_1$;

each $Ar_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, $SO_2$, =N—, —NH—, —N($R_5$)—, and —N($R_9$)— said heterocycle group optionally containing one or more double bonds, said heterocycle group optionally comprising one or more aromatic rings, and said cyclic group optionally being singly or multiply substituted by —$Q_1$;

each $Q_1$ is independently selected from the group consisting of —$NH_2$, —$CO_2H$, —Cl, —F, —Br, —I, —$NO_2$, —CN, =O, —OH, —perfluoro $C_{1-3}$ alkyl, $R_5$, —$OR_5$, —$NHR_5$, $OR_9$, —N($R_9$)($R_{10}$), $R_9$, —C(O)—$R_{10}$, and

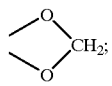

provided that when —$Ar_3$ is substituted with a —$Q_1$ group which comprises one or more additional —$Ar_3$ groups, said additional —$Ar_3$ groups are not substituted with another —$Ar_3$.

More preferred ICE inhibitors of formula (II) are those wherein $R_1$ is (w2) and the other substituents are as described above.

Most preferably in these more preferred ICE inhibitors:
m is 1;
ring C is benzo, pyrido, or thieno;
$R_3$ is selected from the group consisting of —C(O)—H, —C(O)—$Ar_2$, and —C(O)$CH_2$—$T_1$—$R_{11}$;
$R_5$ is selected from the group consisting of:
 —C(O)—$R_{10}$, wherein $R_{10}$ is —$Ar_3$;
 —C(O)O—$R_9$, wherein $R_9$ is —$CH_2$—$Ar_3$;
 —C(O)C(O)—$R_{10}$, wherein $R_{10}$ is —$Ar_3$;
 —$R_9$, wherein $R_9$ is a $C_{1-2}$ alkyl group substituted with —$Ar_3$; and
 —C(O)C(O)—$OR_{10}$, wherein $R_{10}$ is —$CH_2Ar_3$;
$T_1$ is O or S;
$R_6$ is H;
$R_8$ is selected from the group consisting —C(O)—$R_{10}$, —C(O)—$CH_2$—$OR_{10}$, and —C(O)$CH_2$—N($R_{10}$)($R_{10}$) wherein $R_{10}$ is H, $CH_3$, or —$CH_2CH_3$;
$R_{11}$ is selected from the group consisting of —$Ar_4$, —$(CH_2)_{1-3}$—$Ar_4$, and —C(O)—$Ar_4$;
$R_{15}$ is —OH or —$OC_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;
$Ar_2$ is (hh);
Y is O;
each $Ar_3$ cyclic group is independently selected from the set consisting of phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl, and said cyclic group optionally being singly or multiply substituted by —$Q_1$;
each $Ar_4$ cyclic group is independently selected from the set consisting of phenyl, tetrazolyl, naphthyl, pyridinyl, oxazolyl, pyrimidinyl, or indolyl, said cyclic group optionally being singly or multiply substituted by —$Q_1$;

each $Q_1$ is independently selected from the group consisting of —$NH_2$, —Cl, —F, —Br, —OH, —$R_9$, —NH—$R_5$ wherein $R_5$ is —C(O)—$R_{10}$ or —S(O)$_2$—$R_9$, —$OR_5$ wherein $R_5$ is —C(O)—$R_{10}$, —$OR_9$, —N($R_9$)($R_{10}$), and

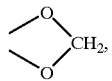

wherein each $R_9$ and $R_{10}$ are independently a —$C_{1-6}$ straight or branched alkyl group optionally substituted with $Ar_3$ wherein $Ar_3$ is phenyl;
provided that when —$Ar_3$ is substituted with a —$Q_1$ group which comprises one or more additional —$Ar_3$ groups, said additional —$Ar_3$ groups are not substituted with another —$Ar_3$.

Other more preferred ICE inhibitors are those wherein $R_1$ is (e10), $X_5$ is CH and the other substituents are as described above.

More preferably, in these more preferred ICE inhibitors $R_3$ is —CO—$Ar_2$ and the other substituents are as described above.

Alternatively, in these more preferred ICE inhibitors, wherein $R_3$ is —C(O)—$CH_2$—$T_1$—$R_{11}$ and $R_{11}$ is —$(CH_2)_{1-3}$—$Ar_4$ and the other substituents are as described above.

Alternatively, in these more preferred ICE inhibitors, $R_3$ is —C(O)—$CH_2$—$T_1$—$R_{11}$, $T_1$ is O, and $R_{11}$, is —C(O)—$Ar_4$ and the other substituents are as described above.

Alternatively, in these more preferred ICE inhibitors, $R_3$ is —C(O)—H and the other substituents are as described above.

Alternatively, in these more preferred ICE inhibitors, $R_3$ is —CO—$CH_2$—$T_1$—$R_{11}$ and $R_{11}$ is —$Ar_4$ and the other substituents are as described above.

Most preferably, in these more preferred ICE inhibitors:
m is 1;
$T_1$ is O or S;
$R_{13}$ is H or a —$C_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;
$R_{21}$ is —H or —$CH_3$;
$R_{51}$ is a $C_{1-6}$ straight or branched alkyl group optionally substituted with $Ar_3$, wherein $Ar_3$ is phenyl, optionally substituted by —$Q_1$;
$Ar_2$ is (hh);
Y is O, and
each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by —$Q_1$;
each $Ar_4$ cyclic group is independently selected from the set consisting of phenyl, tetrazolyl, pyridinyl, oxazolyl, naphthyl, pyrimidinyl, or thienyl, said cyclic group being singly or multiply substituted by —$Q_1$;

each $Q_1$ is independently selected from the group consisting of $-NH_2$, $-Cl$, $-F$, $-Br$, $-OH$, $-R_9$, $-NH-R_5$ wherein $R_5$ is $-C(O)-R_{10}$ or $-S(O)_2-R_9$, $-OR_5$ wherein $R_5$ is $-C(O)-R_{10}$, $-OR_9$, $-NHR_9$, and

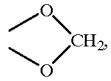

wherein each $R_9$ and $R_{10}$ are independently a $-C_{1-6}$ straight or branched alkyl group optionally substituted with $Ar_3$ wherein $Ar_3$ is phenyl;

provided that when $-Ar_3$ is substituted with a $-Q_1$ group which comprises one or more additional $-Ar_3$ groups, said additional $-Ar_3$ groups are not substituted with another $-Ar_3$.

Other more preferred ICE inhibitors are those wherein $R_1$ is (e10), $X_5$ is N and the other substituents are as described above.

More preferably, in these more preferred ICE inhibitors $R_3$ is $-CO-Ar_2$ and the other substituents are as described above.

Alternatively, in these more preferred ICE inhibitors, $R_3$ is $-C(O)-CH_2-T_1-R_{11}$ and $R_{11}$ is $-(CH_2)_{1-3}-Ar_4$ and the other substituents are as described above.

Alternatively, in these more preferred ICE inhibitors, $R_3$ is $-C(O)-CH_2-T_1-R_{11}$, $T_1$ is O, and $R_{11}$ is $-C(O)-Ar_4$ and the other substituents are as described above.

Alternatively, in these more preferred ICE inhibitors, $R_3$ is $-C(O)-H$ and the other substituents are as described above.

Alternatively, in these more preferred ICE inhibitors, $R_3$ is $-CO-CH_2-T_1-R_{11}$ and $R_{11}$ is $-Ar_4$ and the other substituents are as described above.

Most preferably, in these more preferred ICE inhibitors:

m is 1;

$T_1$ is O or S;

$R_{13}$ is H or a $-C_{1-4}$ straight or branched alkyl group optionally substituted with $-Ar_3$, $-OH$, $-OR_9$, or $-CO_2H$, wherein the $R_9$ is a $-C_{1-4}$ branched or straight alkyl group, wherein $Ar_3$ is morpholinyl or phenyl, wherein the phenyl is optionally substituted with $Q_1$;

$R_{21}$ is $-H$ or $-CH_3$;

$R_{51}$ is a $C_{1-6}$ straight or branched alkyl group optionally substituted with $Ar_3$, wherein $Ar_3$ is phenyl, optionally substituted by $-Q_1$;

$Ar_2$ is (hh);

Y is O, and each $Ar_3$ cyclic group is independently selected from the set consisting of phenyl, naphthyl, thienyl, quinolinyl, isoquinolinyl, pyrazolyl, thiazcolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by $-Q_1$;

each $Ar_4$ cyclic group is independently selected from the set consisting of phenyl, tetrazolyl, pyridinyl, oxazolyl, naphthyl, pyrimidinyl, or thienyl, said cyclic group being singly or multiply substituted by $-Q_1$;

each $Q_1$ is independently selected from the group consisting of $-NH_2$, $-Cl$, $-F$, $-Br$, $-OH$, $-R_9$, $-NH-R_5$ wherein $R_5$ is $-C(O)-R_{10}$ or $-S(O)_2-R_9$, $-OR_5$ wherein $R_5$ is $-C(O)-R_{10}$, $-OR_9$, $-NHR_9$, and

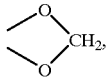

wherein each $R_9$ and $R_{10}$ are independently a $-C_{1-6}$ straight or branched alkyl group optionally substituted with $Ar_3$ wherein $Ar_3$ is phenyl;

provided that when $-Ar_3$ is substituted with a $-Q_1$ group which comprises one or more additional $-Ar_3$ groups, said additional $-Ar_3$ groups are not substituted with another $-Ar_3$.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

In order that this invention be more fully understood, the following examples are set forth. These examples are for the purposes of illustration only and are not to be construed as limiting the scope of the invention in any way.

EXAMPLE 1

ICE Cleaves and Activates pro-IGIF

ICE and ICE Homolog Expression Plasmids

A 0.6 kb cDNA encoding full length murine pro-IGIF (H. Okamura et al., *Nature*, 378, p. 88 (1995) was ligated into the mammalian expression vector pCDLSRα (Y. Takebe et al., *Mol. Cell Biol.*, 8, p. 466 (1988)).

Generally, plasmids (3 μg) encoding active ICE (above), or the three ICE-related enzymes TX, CPP32, and CMH-1 in the pCDLSRα expression vector (C. Faucheu et al., *EMBO*, 14, p. 1914 (1995); Y. Gu et al., *EMBO*, 14, p. 1923 (1995); J. A. Lippke et al., *J. Biol. Chem.*, 271, p. 1825 (1996)), were transfected into subconfluent monolayers of Cos cells in 35-mm dishes using the DEAE-dextran method (Y. Gu et al., *EMBO J.*, 14, p. 1923 (1995)). Twenty-four hours later, cells were lysed and the lysates subjected to SDS-PAGE and immunoblotting using an antiserum specific for IGIF (H. Okamura et al., *Nature*, 378, p. 88 (1995).

Polymerase chain reaction was used to introduce Nde I sites at the 5' and 3' ends of the murine pro-IGIF cDNA using the following primers: GGAATTCCATATGGCTGCCAT-GTCAGAAGAC (forward) (SEQ ID No. 4) and GGT-TAACCATATGCTAACTTTGATGTAAGTTAGTGAG (reverse) (SEQ ID No. 5). The resulting NdeI fragment was ligated into *E. coli* expression vector pET-15B(Novagen) at the NdeI site to create a plasmid that directs the synthesis of a polypeptide of 213 amino acids consisting of a 21-residue peptide (MGSS<u>HHHHHH</u>SS<u>GLVPRGSHM</u> (SEQ ID No. 6), where LVPRGS (SEQ ID No. 7) represents a thrombin cleavage site) fused in-frame to the N-terminus of pro-IGIF at Ala2, as confirmed by DNA sequencing of the plasmid and by N-terminal sequencing of the expressed proteins. *E. coli* strain BL21(DE3) carrying the plasmid was induced with 0.8 mM isopropyl-1-thio-β-D-galactopyranoside for 1.5 hours at 37° C., harvested, and lysed by microfluidization (Microfluidic, Watertown, Mass.) in Buffer A (20 mM sodium phosphate, pH 7.0, 300 mM NaCl, 2 mM dithiothreitol, 10% glycerol, 1 mM phenylmethylsulfonyl fluoride, and 2.5 µg/ml leupeptin). Lysates were cleared by centrifugation at 100,000×g for 30 min. (His)6-tagged pro-IGIF protein was then purified from the supernatant by Ni-NTA-agarose (Qiagen) chromatography under conditions recommended by the manufacturer.

In Vitro pro-IGIF Cleavaae Reactions

In vitro cleavage reactions (30 µl) contained 2 µg of purified pro-IGIF and various concentrations of the purified proteases in a buffer containing 20 mM Hepes, pH 7.2, 0.1% Triton X-100, 2 mM DTT, 1 mM PMSF and 2.5 µg/ml leupeptin and were incubated for 1 hour at 37° C. Conditions for cleavage by granzyme B were as described previously (Y. Gu et al., *J. Biol, Chem.*, 271, p. 10816 (1996)). Cleavage products were analyzed by SDS-PAGE on 16% gels and Coomassie Blue staining, and were subjected to N-terminal amino acid sequencing using an ABI automated peptide sequencer under conditions recommended by the manufacturer.

Kinetic Parameters of IGIF Cleavage by ICE

The kinetic parameters ($k_{cat}/K_M$, $K_M$, and $k_{cat}$) for IGIF cleavage by ICE were determined as follows. $^{35}$S-methionine-labeled pro-IGIF (3000 cpm, prepared by in vitro transcription and translation using, the TNT T7-coupled reticulocyte lysate system (Promega) and pro-IGIF cDNA in a pSP73 vector as template) were incubated in reaction mixtures of 60 µl containing 0.1 to 1 nM recombinant ICE and 190 nM to 12 µM of unlabeled pro-IGIF for 8–10 min at 37° C. Cleavage product concentrations were determined by SDS-PAGE and PhosphoImager analyses. The kinetic parameters were calculated by nonlinear regression fitting of the rate vs. concentration data to the Michaelis-Menten equation using the program Enzfitter (Biosoft).

IFN-γ Induction Assays

A.E7 Th1 cells (H. Quill and R. H. Schwartz, *J. Immunol.*, 138, p. 3704 (1987)) (1.3×10$^5$ cells in 0.15 ml Click's medium supplemented with 10% FBS, 50 µM 2-mercaptoethanol and 50 units/ml IL-2) in 96-well plates were treated with IGIF for 18–20 hours and the culture supernatant were assayed for IFN-γ by ELISA (Endogen, Cambridge, Mass.).

EXAMPLE 2

Processing of pro-IGIF by ICE In Cos Cells

Cos cells were transfected with various expression plasmid combinations as described in Example 1. Transfected Cos cells (3.5×10$^5$ cells in a 35-mm dish) were labeled for 7 hours with 1 ml of methionine-free DMEM containing 2.5% normal DMEM, 1% dialyzed fetal bovine serum and 300 µCi/ml $^{35}$S-methionine ($^{35}$S-Express Protein Labeling-Mix, New England Nuclear). Cell lysates (prepared in 20 mM Hepes, pH 7.2, 150 mM NaCl, 0.1% Triton X-100, 5 mM N-ethylmaleimide, 1 mM PMSF, 2.5 µg/ml leupeptine) or conditioned medium were immunoprecipitated with an antiIGIF antibody that recognizes both the precursor and the mature forms of IGIF (H. Okamura et al., *Nature*, 378, p. 88 (1995)). Immunoprecipitated proteins were analyzed by SDS-PAGE (polyacrylamide gel electrophoresis) and fluorography (FIG. 2A).

We also measured the presence of IFN-γ inducing activity in the cell lysates and the conditioned media of transfected cells (FIG. 2B). Transfected Cos cells (3.5×10$^5$ cells in a 35-mm dish) were grown in 1 ml medium for 18 hours. Media was harvested and used at 1:10 final dilution in the IFN-γ induction assay (Example 1). Cos cell pellets from the same transfection were lysed in 100 µl of 20 mM Hepes, pH 7.0, by freeze-thawing 3 times. Lysates were cleared by centrifugation as described above and were used at a 1:10 dilution in the assay.

EXAMPLE 3

IGIF is a Physiological Substrate of ICE

Wild type (ICE+/+) and ICE-/- mice were primed with heat-inactivated *P. acnes*, and Kupffer cells were isolated from these mice 7 days after priming and were then challenged with 1 µg/nl LPS for 3 hours. The amounts of IGIF in the conditioned media were measured by ELISA.

Wild type or ICE-deficient mice were injected intraperitoneally with heat-killed *p. acnes* as described (H. Okamura et al., *Infection and Immunity*, 63, p. 3966 (1995)). Kupffer cells were prepared seven days later according to Tsutsui et al. (H. Tsutsui et al., *Hepato-Gastroenterol.*, 39, p. 553 (1992)) except a nycodenz gradient was used instead of metrizamide. For each experiment, Kupffer cells from 2-3 animals were pooled and cultured in RPMI 1640 supplemented with 10% fetal calf serum and 1 µg/ml LPS. Cell lysates and conditioned medium were prepared 3 hours later.

Kupffer cells from wild type and ICE-/- mice were metabolically labeled with $^{35}$S-methionine as for Cos cells (described above in Example 2) except that methionine-free RPMI 1640 was used in place of DMEM. IGIF immunoprecipitation experiments were performed on cell lysates and conditioned media and immunoprecipitates were analyzed by SDS-PAGE and fluorography as described in Example 1. See FIG. 3.

EXAMPLE 4

Induction of IFN-γ Production In Vivo

LPS mixed with 0.5% carboxymethyl cellulose in PBS, pH 7.4, was administered to mice by intraperitoneal injection (30 mg/kg LPS) in a dose volume of 10 ml/kg. Blood was collected every 3 h for 24 h from groups of three ICE-deficient or wild type mice. Serum IFN-γ levels were determined by ELISA (Endogen).

EXAMPLE 5

Human PBMC Assays

Buffy coat cells were obtained from blood donors and peripheral blood mononuclear cells (PBMC) were isolated by centrifugation in LeukoPrep tubes (Becton-Dickinson, Lincoln Park, N.J.). PBMC were added (3×10$^6$/well) to 24 well Corning tissue culture plates and after 1 hr incubation at 37° C., non-adherent cells were removed by gently washing. Adherent mononuclear cells were stimulated with LPS (1 µg/ml) with or without ICE inhibitor in 2 ml RPMI-1640-10% FBS. After 16–18 hr incubation at 37° C., IGIF and IFN-γ were quantitated in culture supernatants by ELISA.

EXAMPLE 6

ICE Inhibition Assays

We obtained inhibition constants ($K_i$) and IC$_{50}$ values for compounds of this invention using the three methods described below:

1. Enzyme Assay with UV-visible Substrate

This assay was run using an Succinyl-Tyr-Val-Ala-Asp-pNitroanilide substrate (SEQ ID No. 8). Synthesis of analogous substrates is described by L. A. Reiter (Int. J. Peptide Protein Res. 43, 87–96 (1994)). The assay mixture contained:

65 μl buffer (10 mM Tris, 1 mM DTT, 0.1% CHEPS @pH 8.1)
   10 μl ICE (50 nM final concentration to give a rate of ~1 mOD/min)
   5 μl DMSO/Inhibitor mixture
   20 μl 400 μM Substrate (80 μM final concentration)
   100 μl total reaction volume The visible ICE assay was run in a 96-well microtiter plate. Buffer, ICE and DMSO (if inhibitor is present) were added to the wells in the order listed. The components were left to incubate at room temperature for 15 minutes starting at the time that all components were present in all wells. The microtiter plate reader was set to incubate at 37° C. After the 15 minute incubation, substrate was added directly to the wells and the reaction monitored by following the release of the chromophore (pNA) at 405–603 nm at 37° C. for 20 minutes. A linear fit of the data was performed and the rate calculated in mOD/min. DMSO was only present during experiments involving inhibitors, buffer was used to make up the volume to 100 μl in the other experiments.

2. Enzyme Assay with Fluorescent Substrate

This assay was run essentially according to Thornberry et al. (Nature 356: 768–774 (1992)), using substrate 17 referenced in that article. The substrate was: Acetyl-Tyr-Val-Ala-Asp-amino-4-methylcoumarin (AMC) (SEQ ID No. 9). The following components were mixed:

65 μl buffer(10 mM Tris, 1 mM DTT, 0.1% CHAPS (@pH8.1)
   10 μl ICE (2–10 nM final concentration)
   5 μl DMSO/inhibitor solution
   20 μl 150 μM Substrate (30 μM final)
   100 μl total reaction volume The assay was run in a 96-well microtiter plate. Buffer and ICE were added to the wells. The components were left to incubate at 37° C. for 15 minutes in a temperature-controlled wellplate. After the 15 minute incubation, the reaction was started by adding substrate directly to the wells and the reaction monitored at 37° C. for 30 minutes by following the release of the AMC fluorophore using an excitation wavelength for 380 nm and an emission wavelength of 460 nm. A linear fit of the data for each well was performed and a rate determined in fluorescence units per second.

For determination of enzyme inhibition constants ($K_i$) or the mode of inhibition (competitive, uncompetitive or noncompetitive), the rate data determined in the enzyme assays at varying inhibitor concentrations were computer-fit to standard enzyme kinetic equations (see I. H. Segel, *Enzyme Kinetics*, Wiley-Interscience, 1975).

The determination of second order rate constants for irreversible inhibitors was performed by fitting the fluorescence vs time data to the progress equations of Morrison. Morrison, J. F., *Mol. Cell. Biophys.*, 2, pp. 347–368 (1985). Thornberry et al. have published a description of these methods for measurement of rate constants of irreversible inhibitors of ICE. Thornberry, N. A., et al. *Biochemistry*, 33, pp. 3923–3940 (1994). For compounds where no prior complex formation can be observed kinetically, the second order rate constants ($k_{inact}$) were derived directly from the slope of the linear plots of $k_{obs}$ vs. [I]. For compounds where prior complex formation to the enzyme could be detected, the hyperbolic plots of $k_{obs}$ vs. [I] were fit to the equation for saturation kinetics to first generate $K_i$ and k'. The second order rate constant $k_{inact}$ is then given by k'/$K_i$.

3. PBMC Cell Assay

IL-1β or IGIF Assay with a Mixed Population of Human Peripheral Blood Mononuclear Cells (PBMC) or Enriched Adherent Mononuclear Cells Processing of pre-IL-1β or pro-IGIF by ICE can be measured in cell culture using a variety of cell sources. Human PBMC obtained from healthy donors provides a mixed population of lymphocyte subtypes and mononuclear cells that produce a spectrum of interleukins and cytokines in response to many classes of physiological stimulators. Adherent mononuclear cells from PBMC provide an enriched source of normal monocytes for selective studies of cytokine production by activated cells.

Experimental Procedure:

An initial dilution series of test compound in DMSO or ethanol was prepared, with a subsequent dilution into RPMI-10% FBS media (containing 2 mM L-glutamine, 10 mM HEPES, 50 U and 50 μg/ml pen/strep) respectively to yield drugs at 4× the final test concentration containing 0.4% DMSO or 0.4% ethanol. The final concentration of DMSO was 0.1% for all drug dilutions. A concentration titration which brackets the apparent $K_i$ for a test compound determined in an ICE inhibition assay was generally used for the primary compound screen.

Generally 5-6 compound dilutions were tested and the cellular component of the assay was performed in duplicate, with duplicate ELISA determinations on each cell culture supernatant.

PBMC Isolation and IL-1 or IGIF Assay:

Buffy coat cells isolated from one pint of human blood (yielding 40–45 ml final volume plasma plus cells) were diluted with media to 80 ml and LeukoPREP separation tubes (Becton Dickinson) and each were overlaid with 10 ml of cell suspension. After 15 min centrifugation at 1500–1800×g, the plasma/media layer was aspirated and then the mononuclear cell layer was collected with a Pasteur pipette and transferred to a 15 ml conical centrifuge tube (Corning). Media was added to bring the volume to 15 ml, the cells gently mixed by inversion and centrifuged at 300×g for 15 min. The PBMC pellet was resuspended in a small volume of media, cells counted and adjusted to $6 \times 10^6$ cells/ml.

For the cellular assay, 1.0 ml of the cell suspension was added to each well of a 24-well flat bottom tissue culture plate (Corning), 0.5 ml test compound dilution and 0.5 ml LPS solution (Sigma #L-3012; 20 ng/ml solution prepared in complete RPMI media; final LPS concentration 5 ng/ml). The 0.5 ml additions of test compound and LPS are usually sufficient to mix the contents of the wells. Three control mixtures were run per experiment, with either LPS alone, solvent vehicle control, and/or additional media to adjust the final culture volume to 2.0 ml. The cell cultures were incubated for 16–18 hr at 37° C. in the presence of 5% $CO_2$.

At the end of the incubation period, cells were harvested and transferred to 15 ml conical centrifuge tubes. After centrifugation for 10 min at 200×g, supernatants were harvested and transferred to 1.5 ml Eppendorf tubes. It may be noted that the cell pellet may be utilized for a biochemical evaluation of pre-IL-1β or pro-IGIF and/or mature IL-1β or IGIF content in cytosol extracts by Western blotting or ELISA with pre-IL-1β and/or IGIF-specific antisera.

Isolation of Adherent Mononuclear cells:

PBMC were isolated and prepared as described above. Media (1.0 ml) was first added to wells followed by 0.5 ml of the PBMC suspension. After a one hour incubation, plates were gently shaken and nonadherent cells aspirated from each well. Wells were then gently washed three times with 1.0 ml of media and finally resuspended in 1.0 ml media. The enrichment for adherent cells generally yields 2.5–3.0× $10^5$ cells per well. The addition of test compounds, LPS, cell incubation conditions and processing of supernatants proceeds were as described above.

ELISA:

We have used Quantikine kits (R&D Systems) for measurement of mature IL-1β or IGIF. Assays were performed according to the manufacturer's directions. Mature IL-1β levels of about 1–3 ng/ml in both PBMC and adherent mononuclear cell positive controls were observed. ELISA assays were performed on 1:5, 1:10 and 1:20 dilutions of supernatants from LPS-positive controls to select the optimal dilution for supernatants in the test panel.

The inhibitory potency of the compounds can be represented by an $IC_{50}$ value, which is the concentration of inhibitor at which 50% of mature IL-1β or IGIF is detected in the supernatant as compared to the positive controls.

For example, we obtained the following data for compound 412 of this invention using the methods described. (The structure of compound 412 is shown further below).

| Compound | UV-Visible Ki (nM) | Cell PBMC avg. IC50 (nM) |
|---|---|---|
| 412 | 1.3 | 580 |

The preparation of compound 412 is described below. Other ICE inhibitors may be prepared in a similar manner. The preparation of ICE inhibitors may also be found in the references cited and incorporated by reference herein.

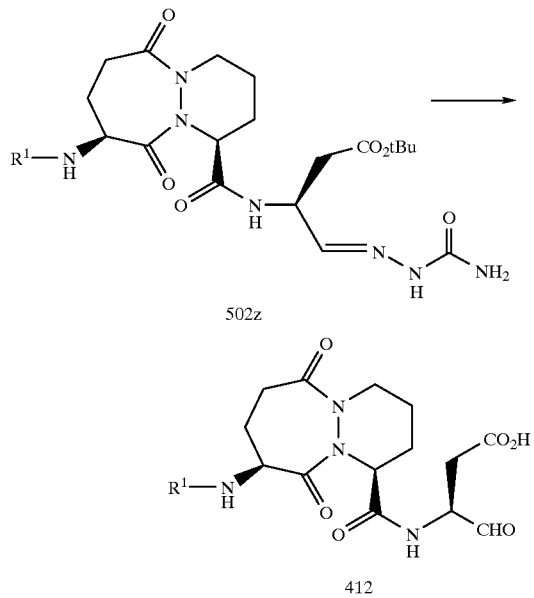

| compound | R¹ |
|---|---|
| 502z, 412 | (isoquinolin-1-yl carbonyl structure) |

[3S(1S,9S)] t-Butyl 3-[6,10-dioxo-9-(isoquinolin-1-oylamino)-1,2,3,4,7,8,9,10-octahydro-6H-pyridazino[1,2-a][1,2]-diazepine-1-carboxamido]-4-oxobutanoate semicarbazone (502z), (3S)-3-(1-Fluorenylmethyloxycarbonylamino)-4-oxobutyric acid tert-butyl ester semicarbazone (210 mg, 0.4 mol, Prepared in a similar manner to the benzyloxycarbonyl analog in Graybill et al., *Int. J. Protein Res.*, 44, pp. 173–82 (1994).) was dissolved in 10 ml of DMF and 2 ml of diethylamine and stirred for 2 h. The reaction was concentrated in vacuo to give (3S)-3-amino-4-oxobutyric acid tert-butyl ester semicarbazone. The 0° C. solution of the above residue and the acid corresponding to 502z (200 mg, 0.42 mmol) in 5 ml of DMF and 5 ml of $CH_2Cl_2$ was treated with 1-hydroxybenzotriazole (57 mg, 0.42 mmol) and 1-(3-dimethylaminopropyl)-3-ethylcarbodiimide hydrochloride (98 mg, 0.51 mmol). The reaction was stirred at RT for 18 h, poured onto EtOAc (75 ml) and washed with aq. 0.3 N $KHSO_4$, sat. aq. $NaHCO_3$ and sat. aq. NaCl, dried over $NaSO_4$ and concentrated in vacuo to afford a pale yellow solid (90%): mp. 142–145° C.; $[\alpha]_D^{24}$-136.5° (c 0.06, $CH_2Cl_2$); $^1H$ NMR ($CDCl_3$) δ 9.51–9.46 (1H, m), 9.11 (1H, s), 8.83 (1H, d, J=7.8), 8.53 (1H, d, J=5.5), 7.89–7.83 (2H, m), 7.77–7.65 (2H, m), 7.55 (1H, d, J=7.2), 7.18 (1H, d, J=2.7), 5.26–5.12 (2H, m), 4.87 (1H, m), 4.59 (1H, m), 3.25–3.12 (2H, m), 2.95–2.76 (2H, m), 2.59–2.38, 2.18–1.94, 1.70 (5H, 3m), 1.44 (9H, s).

[3S(1S,9S)] 3-[6,10-Dioxo-9-(isoquinolin-1-oylamino)-1,2,3,4,7,8,9,10-octahydro-6H-pyridazino[1,2-a][1,2]-diazepine-1-carboxamido]-4-oxobutanoic acid (412). 412 was stirred with 10 ml of 33% $TFA/H_2O$ for 4 h and concentrated in vacuo. The residue was dissolved in 7 ml of MeOH/acetic acid/37% aq. formaldehyde (5:1:1) and stirred for 18 h to afford a white glassy solid (69%): mp. 138–141° C.; $[\alpha]_D^{23}$-105.5° (c 0.5, $CH_2Cl_2$); IR (KBr) 3375, 1787, 1659, 1515, 1421, 1278, 1256; $^1H$ NMR ($CDCl_3$) δ 9.32 (1H, m), 8.79 (1H, m), 8.47 (1H, m), 7.86–7.64 (4H, m), 5.31, 5.18, 4.59, 4.37 (4 or 5H, m), 3.55–2.76, 2.49–2.39, 2.05, 1.65 (11H, 4m). Anal. Calcd for $C_{24}H_{25}N_5O_7 \cdot 1.5H_2O$: C, 55.17; H, 5.40; N, 13.40. Found: C, 54.87; H, 5.22; N, 13.15. MS ($ES^+$, m/z) 494 ($M^+$-1, 100%).

What is claimed is:

1. A method for decreasing IGIF production in a subject comprising the step of administering to the subject a pharmaceutical composition comprising a therapeutically effective amount of an ICE inhibitor and a pharmaceutically acceptable carrier.

2. A method for decreasing IFN-γ production in a subject comprising the step of administering to the subject a pharmaceutical composition comprising a therapeutically effective amount of an ICE inhibitor and a pharmaceutically acceptable carrier.

3. The method according to claims 1 or 2 wherein the ICE inhibitor is a compound represented by formula (I):

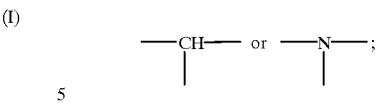

(I)

wherein:
R₁ is selected from the group consisting of the following formulae:

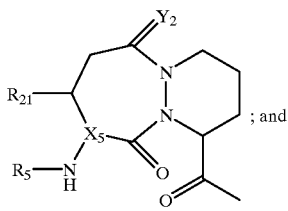

(e10)

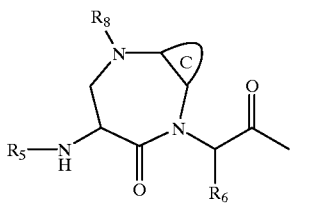

(w2)

ring C is chosen from the group consisting of benzo, pyrido, thieno, pyrrolo, furano, thiazolo, isothiazolo oxazolo, isoxazolo, pyrimido, imidazolo, cyclopentyl and cyclohexyl;

R₂ is:

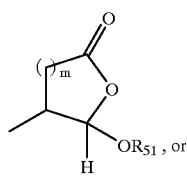

(a)

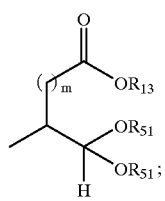

(b)

m is 1 or 2;
each $R_5$ is independently selected from the group consisting of:
—(O)—$R_{10}$,
—C(O)O—$R_9$,
—C(O)—N($R_{10}$)($R_{10}$)
—S(O)₂—$R_9$,
—S(O)₂—NH—$R_{10}$,
—C(O)—CH₂—O—$R_9$,
—C(O)C(O)—$R_{10}$,
—$R_9$,
—H,
—C(O)C(O)—O$R_{10}$, and
—C(O)C(O)—N($R_9$)($R_{10}$);

$X_5$ is

—CH— or —N—;

$Y_2$ is H₂ or O;
$R_6$ is selected from the group consisting of —H and —CH₃;
$R_8$ is selected from the group consisting of:
—C(O)—$R_{10}$,
—C(O)O—$R_9$,
—C(O)—N(H)—$R_{10}$,
—S(O)₂—$R_9$,
—S(O)₂—NH—$R_{10}$,
—C(O)—CH₂—O$R_{10}$,
—C(O)C(O)—$R_{10}$;
—C(O)—CH₂N($R_{10}$)($R_{10}$),
—C(O)—CH₂C(O)—O—$R_9$,
—C(O)—CH₂C(O)—$R_9$,
—H, and
—C(O)—C(O)—O$R_{10}$;
each $R_9$ is independently selected from the group consisting of —Ar₃ and a —$C_{1-6}$ straight or branched alkyl group that is optionally substituted with Ar₃, wherein the —$C_{1-6}$ alkyl group is optionally unsaturated;
each $R_{10}$ is independently selected from the group consisting of —H, —Ar₃, a $C_{3-6}$ cycloalkyl group, and a —$C_{1-6}$ straight or branched alkyl group optionally substituted with Ar₃, wherein the —$C_{1-6}$ alkyl group is optionally unsaturated;
$R_{13}$ is selected from the group consisting of H, Ar₃, and a $C_{1-6}$ straight or branched alkyl group that is optionally substituted with Ar₃, —CONH₂, —OR₅, —OH, —OR₉, or —CO₂H;
each $R_{51}$, is independently selected from the group consisting of $R_9$, —C(O)—$R_9$, —C(O)—N(H)—$R_9$, or each $R_{51}$ taken together forms a saturated 4–8 member carbocyclic ring or hterocyclic ring containing —O—, —S—, or —NH—;
each $R_{21}$ is independently selected from the group consisting of —H or a —$C_{1-6}$ straight or branched alkyl group;
each Ar₃ is a cyclic group independently selected from the set consisting of an aryl group which contains 6, 10, 12, or 14 carbon atoms and between 1 and 3; rings; any an aromatic heterocycle group containing between 5 and 15 ring atoms and between 1 and 3 rings, said heterocyclic group containing at least one heteroatom group selected from —O—, —S—, —SO—, SO₂, =N—, and —NH—, said heterocycle group optionally containing one or more double bonds, said heterocycle group optionally comprising one or more aromatic rings, and said cyclic group optionally being singly or multiply substituted by —$Q_1$;
each $Q_1$ is independently selected from the group consisting of —NH₂, —CO₂H, —Cl, —F, —Br, —I, —NO₂, —CN, =O, —OH, —perfluoro $C_{1-6}$ alkyl, $R_5$, —OR₅, —NHR₅, OR₉, —N($R_9$)($R_{10}$), $R_9$, —C(O)—$R_{10}$, and

provided that when —Ar₃ is substituted with a —Q₁ group which comprises one or more additional —Ar₃ groups, said additional —Ar₃ groups are not substituted with anothqr —Ar₃.

4. The method according to claims 1 or 2, wherein the ICE inhibitor is a compound represented by formula (II):

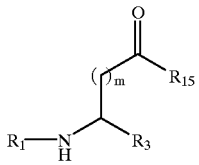

(II)

wherein:

m is 1 or 2;

R₁ is selected from the group consisting of the following formulae:

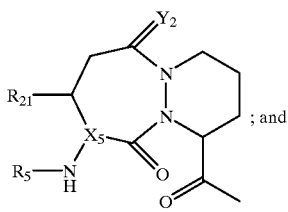

(e10)

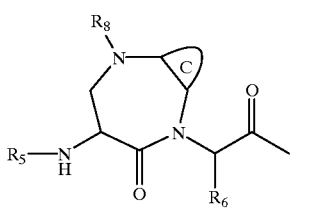

(w2)

ring C is chosen from the group consisting of benzo, pyrido, thieno, pyrrolo, furano, thiazolo, isothiazol, oxazolo, isoxazolo, pyrimido, imidazolo, cyclopenty, and cyclohexyl;

R₃ is selected from the group consisting of:
—CN,
—C(O)—H,
—C(O)—CH₂—T₁—R₁₁,
—C(O)—CH₂—F,
—C=N—O—R₉, and
—CO—Ar₂;

each R₅ is independently selected from the group consisting of:
—C(O)—R₁₀,
—C(O)O—R₉,
—C(O)—N(R₁₀)(R₁₀)
—S(O)₂—R₉,
—S(O)₂—NH—R₁₀,
—C(O)—CH₂—O—R₉,
—C(O)C(O)—R₁₀,
—R₉,
—H,
—C(O)C(O)—OR₁₀, and
—C(O)C(O)—N(R₉)(R₁₀);

X, is

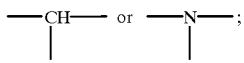

Y₂ is H₂ or O;

each T₁ is independently selected from the group consisting of —O—, —S—, —S(O)—, and —S(O)₂—;

R₆ is selected from the group consisting of —H and —CH₃;

R₈ is selected from the group consisting of:
—C(O)—R₁₀,
—C(O)O—R₉,
—C(O)—NH—R₁₀,
—S(O)₂—R₉,
—S(O)₂—NH—R₁₀,
—C(O)—CH₂—OR₁₀,
—C(O)C(O)—R₁₀,
—C(O)—CH₂—N(R₁₀)(R₁₀)
—C(O)—CH₂C(O)—O—R₉,
—C(O)—CH₂C(O)—R₉,
—H, and
—C(O)—C(O)—OR₁₀;

each R₉ is independently selected from the group consisting of —Ar₃ and a —C₁₋₆ straight or branched alkyl group that is optionally substituted with Ar₃, wherein the —C₁₋₆ alkyl group is optionally unsaturated;

each R₁₀ is independently selected from the group consisting of —H, —Ar₃, a C₃₋₆ cycloalkyl group, and a —C₁₋₆ straight or branched alkyl group optionally substituted with Ar₃, wherein the —C₁₋₆ alkyl group is optionally unsaturated;

each R₁₁ is independently selected from the group consisting of:
—Ar₄,
—(CH₂)₁₋₃—Ar₄,
—H, and
—C(O)—Ar₄;

R₁₅ is selected from the group consisting of —OH, —OAr₃, —N(H)—OH, and a —OC₁₋₆ straight or branched alkyl group opticnally substituted with —Ar₃, —CONH₂, —OR₅, —OH, —OR₉, or —CO₂H;

each R₂₁ is independently selected from the group consisting of —H or a —C₁₋₆ straight or branched alkyl group;

Ar₂ is independently selected from the following group, in which any ring may optionally be singly or multiply substituted by —Q₁:

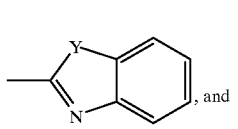

(hh)

-continued

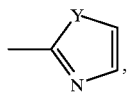
(ii)

wherein each Y is independently selected from the group consisting of O and S;

each $Ar_3$ is a cyclic group independently selected from the set consisting of an aryl group which contains 6, 10, 120 or 14 carbon atoms and between 1 and 3 rings; and an aromatic heterocycle group containing between 5 and 15 ring atoms and between 1 and 3 rings, said heterocyclic group containing at least one heteroaton group selected from —C—, —S—, —SO—, $SO_2$, =N—, and —NH—, —N($R_5$)—, and —N($R_9$)— said heterocycle group optionally containing one or more double bonds, said heterocycle group optionally comprising one or more aromatic rings, and said cyclic group optionally being singly or multiply substituted by —$Q_1$;

each $Ar_4$ is a cyclic group independently selected from the set consisting of an aryl group that contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, $SO_2$, =N—, —NH—, —N($R_5$)—, and —N($R_9$)— said heterocycle group optionally containing one or more double bonds, said heterocycle group optionally comprising one or more aromatic rings, and said cyclic group optionally being singly or multiply substituted by —$Q_1$;

each $Q_1$ is independently selected from the group consisting of —$NH_2$, —$CO_2H$, —Cl, —F, —Br, —I, —$NO_2$, —CN, =O, —OH, —perfluoro $C_{1-3}$ alkyl, $R_5$, —$OR_5$, —$NHR_5$, $OR_9$, —N($R_9$)($R_{10}$), $R_9$, —C(O)—$R_{10}$, and

provided that when —$Ar_3$ is substituted with a —$Q_1$ group which comprises one or more additional —$Ar_3$ groups, said additional —$Ar_3$ groups are not substituted with another —$Ar_3$.

5. The method according to claim 4, wherein $R_1$ is (w2).

6. The method according to claim 4, wherein $R_1$ is (e10) and $X_5$ is CH.

7. The method according to claim 6, wherein $R_3$ is CO—$Ar_2$.

8. The method according to claim 6, wherein $R_3$ is —C(O)—$CH_2$—$T_1$—$R_{11}$ and $R_{11}$ is —$(CH_2)_{1-3}$—$Ar_4$.

9. The method according to claim 6, wherein $R_3$ is —C(O)—$CH_2$—$T_1$—$R_{11}$, $T_1$ is O, and $R_{11}$ is —C(O)—$Ar_4$.

10. The method according to claim 6, wherein $R_3$ is —C(O)—H.

11. The method according to claim 6, wherein $R_3$ is —CO—$CH_2$—$T_1$—$R_{11}$ and $R_{11}$ is —$Ar_4$.

12. The method according to claim 4, wherein $R_1$ is (e10) and $X_5$ is N.

13. The method according to claim 12, wherein $R_3$ is CO—$Ar_2$.

14. The method according to claim 12, wherein $R_3$ is —C(O)—$CH_2$—$T_1$—$R_{11}$ and $R_{11}$ is —$(CH_2)_{1-3}$—$Ar_4$.

15. The method according to claim 12, wherein $R_3$ is —C(O)—$CH_2$—$T_1$—$R_{11}$, $T_1$ is O, and $R_{11}$ is —C(O)—$Ar_4$.

16. The method according to claim 12, wherein $R_3$ is —C(O)—H.

17. The method according to claim 12, wherein $R_3$ is —CO—$CH_2$—$T_1$—$R_{11}$ and $R_{11}$ is —$Ar_4$.

* * * * *